US010344092B2

(12) United States Patent
Johnson et al.

(10) Patent No.: US 10,344,092 B2
(45) Date of Patent: Jul. 9, 2019

(54) BI-SPECIFIC MONOVALENT FC DIABODIES THAT ARE CAPABLE OF BINDING CD32B AND CD79B AND USES THEREOF

(71) Applicant: MacroGenics, Inc., Rockville, MD (US)

(72) Inventors: Leslie S. Johnson, Darnestown, MD (US); Ling Huang, Bethesda, MD (US); Kalpana Shah, Boyds, MD (US); Ezio Bonvini, Potomac, MD (US); Paul A. Moore, Bethesda, MD (US); Wei Chen, Gaithersburg, MD (US)

(73) Assignee: MacroGenics, Inc., Rockville, MD (US)

( * ) Notice: Subject to any disclaimer, the term of this patent is extended or adjusted under 35 U.S.C. 154(b) by 384 days.

(21) Appl. No.: 14/909,820

(22) PCT Filed: Aug. 6, 2014

(86) PCT No.: PCT/US2014/049848
§ 371 (c)(1),
(2) Date: Feb. 3, 2016

(87) PCT Pub. No.: WO2015/021089
PCT Pub. Date: Feb. 12, 2015

(65) Prior Publication Data
US 2016/0194396 A1 Jul. 7, 2016

Related U.S. Application Data

(60) Provisional application No. 61/864,217, filed on Aug. 9, 2013, provisional application No. 61/866,416, filed on Aug. 15, 2013, provisional application No. 61/869,519, filed on Aug. 23, 2013, provisional application No. 61/907,525, filed on Nov. 22, 2013.

(51) Int. Cl.
| | |
|---|---|
| *C07K 16/00* | (2006.01) |
| *C12P 21/08* | (2006.01) |
| *A61K 39/395* | (2006.01) |
| *A61K 39/40* | (2006.01) |
| *C07K 16/28* | (2006.01) |
| *C07K 16/46* | (2006.01) |
| *A61K 39/00* | (2006.01) |

(52) U.S. Cl.
CPC ........ *C07K 16/283* (2013.01); *C07K 16/2803* (2013.01); *C07K 16/468* (2013.01); *A61K 2039/505* (2013.01); *C07K 2317/31* (2013.01); *C07K 2317/52* (2013.01); *C07K 2317/60* (2013.01); *C07K 2317/624* (2013.01); *C07K 2317/73* (2013.01); *C07K 2317/74* (2013.01); *C07K 2319/31* (2013.01); *C07K 2319/73* (2013.01)

(58) Field of Classification Search
None
See application file for complete search history.

(56) References Cited

U.S. PATENT DOCUMENTS

| | | |
|---|---|---|
| 4,526,938 A | 7/1985 | Churchill et al. |
| 4,752,601 A | 6/1988 | Hahn |
| 4,800,078 A | 1/1989 | Prince et al. |
| 4,980,286 A | 12/1990 | Morgan et al. |
| 5,116,964 A | 5/1992 | Capon et al. |
| 5,128,326 A | 7/1992 | Balazs et al. |
| 5,169,933 A | 12/1992 | Anderson et al. |
| 5,290,540 A | 3/1994 | Prince et al. |
| 5,348,876 A | 9/1994 | Michaelson et al. |
| 5,576,184 A | 11/1996 | Better et al. |
| 5,585,089 A | 12/1996 | Queen et al. |
| 5,624,821 A | 4/1997 | Winter et al. |
| 5,648,260 A | 7/1997 | Winter et al. |
| 5,679,377 A | 10/1997 | Bernstein et al. |
| 5,698,449 A | 12/1997 | Baumann et al. |
| 5,723,584 A | 3/1998 | Schatz |

(Continued)

FOREIGN PATENT DOCUMENTS

| | | |
|---|---|---|
| EP | 0327378 | 8/1989 |
| EP | 1354600 | 10/2003 |

(Continued)

OTHER PUBLICATIONS

US 6,331,391 B1, 12/2001, Wittrup et al. (withdrawn)
Veri et al. Arthritis & Rheumatism. 62;7:1933-1943 (Year: 2010).*
Agliano, A. et al. (2008) "Human Acute Leukemia Cells Injected in NOD/Ltsz-Scid/IL-2gamma Null Mice Generate a Faster and More Efficient Disease Compared to Other NOD/Scid-Related Strains," Int. J. Cancer 123(9):222-2227.
Akbulut, S. et al. (2012) "Graft-Versus-Host Disease After Liver Transplantation: A Comprehensive Literature Review," World J. Gasteroenterol. 18(37):5240-5248.

(Continued)

*Primary Examiner* — Chun W Dahle
(74) *Attorney, Agent, or Firm* — William C. Schrot; Jeffrey I. Auerbach; AuerbachSchrot LLC

(57) ABSTRACT

The present invention is directed to bi-specific monovalent diabodies that comprise an immunoglobulin Fc Domain ("bi-specific monovalent Fc diabodies") and are composed of three polypeptide chains and which possess at least one binding site specific for an epitope of CD32B and one binding site specific for an epitope of CD79b (i.e., a "CD32B×CD79b bi-specific monovalent Fc diabody"). The bi-specific monovalent Fc diabodies of the present invention are capable of simultaneous binding to CD32B and CD79b. The invention is directed to such compositions, to pharmaceutical compositions that contain such bi-specific monovalent Fc diabodies and to methods for their use in the treatment of inflammatory diseases or conditions, and in particular, systemic lupus erythematosus (SLE) and graft vs. host disease.

9 Claims, 8 Drawing Sheets

Specification includes a Sequence Listing.

(56) References Cited

U.S. PATENT DOCUMENTS

| | | |
|---|---|---|
| 5,736,135 A | 4/1998 | Goeddel et al. |
| 5,736,137 A | 4/1998 | Anderson et al. |
| 5,855,913 A | 1/1999 | Hanes et al. |
| 5,874,064 A | 2/1999 | Edwards et al. |
| 5,874,239 A | 2/1999 | Schatz |
| 5,912,015 A | 6/1999 | Bernstein et al. |
| 5,916,597 A | 6/1999 | Lee et al. |
| 5,932,433 A | 8/1999 | Schatz |
| 5,934,272 A | 8/1999 | Lloyd et al. |
| 5,945,115 A | 8/1999 | Dunn et al. |
| 5,985,309 A | 11/1999 | Edwards et al. |
| 5,985,320 A | 11/1999 | Edwards et al. |
| 5,985,599 A | 11/1999 | Mckenzie et al. |
| 5,989,463 A | 11/1999 | Tracy et al. |
| 6,019,968 A | 2/2000 | Platz et al. |
| 6,025,485 A | 2/2000 | Kamb et al. |
| 6,114,147 A | 9/2000 | Frenken et al. |
| 6,165,745 A | 12/2000 | Ward et al. |
| 6,194,551 B1 | 2/2001 | Idusogie et al. |
| 6,242,195 B1 | 6/2001 | Idusogie et al. |
| 6,277,375 B1 | 8/2001 | Ward |
| 6,300,065 B1 | 10/2001 | Kieke et al. |
| 6,423,538 B1 | 7/2002 | Wittrup et al. |
| 6,455,263 B2 | 9/2002 | Payan |
| 6,492,123 B1 | 12/2002 | Holliger et al. |
| 6,528,624 B1 | 3/2003 | Idusogie et al. |
| 6,538,124 B1 | 3/2003 | Idusogie et al. |
| 6,613,884 B1 | 9/2003 | Johansson et al. |
| 6,623,940 B1 | 9/2003 | Ledbetter et al. |
| 6,737,056 B1 | 5/2004 | Presta |
| 6,821,505 B2 | 11/2004 | Ward |
| 7,122,646 B2 | 10/2006 | Holliger et al. |
| 7,315,786 B2 | 1/2008 | Dahiyat et al. |
| 7,317,091 B2 | 1/2008 | Lazar et al. |
| 7,355,008 B2 | 4/2008 | Stavenhagen et al. |
| 7,425,619 B2 | 9/2008 | Koenig et al. |
| 7,521,542 B2 | 4/2009 | Johnson et al. |
| 7,632,497 B2 | 12/2009 | Stavenhagen |
| 7,700,100 B2 | 4/2010 | Johnson et al. |
| 7,786,270 B2 | 8/2010 | Johnson et al. |
| 7,960,512 B2 | 6/2011 | Stavenhagen et al. |
| 8,003,774 B2 | 8/2011 | Stavenhagen et al. |
| 8,044,180 B2 | 10/2011 | Koenig et al. |
| 8,133,982 B2 | 3/2012 | Johnson et al. |
| 8,187,593 B2 | 5/2012 | Koenig et al. |
| 8,192,737 B2 | 6/2012 | Stavenhagen et al. |
| 8,193,318 B2 | 6/2012 | Koenig et al. |
| 8,216,574 B2 | 7/2012 | Stavenhagen et al. |
| 8,216,579 B2 | 7/2012 | Johnson et al. |
| 8,217,147 B2 | 7/2012 | Stavenhagen et al. |
| 8,445,645 B2 | 5/2013 | Stavenhagen et al. |
| 8,586,713 B2 | 11/2013 | Davis et al. |
| 8,642,743 B2 | 2/2014 | Herne |
| 2003/0077282 A1 | 4/2003 | Bigler et al. |
| 2003/0158389 A1 | 8/2003 | Idusogie et al. |
| 2004/0002587 A1 | 1/2004 | Watkins et al. |
| 2004/0038339 A1 | 2/2004 | Kuffer et al. |
| 2004/0058400 A1 | 3/2004 | Holliger et al. |
| 2004/0110226 A1 | 6/2004 | Lazar et al. |
| 2004/0132101 A1 | 7/2004 | Lazar et al. |
| 2004/0185045 A1 | 9/2004 | Koenig et al. |
| 2004/0220388 A1 | 11/2004 | Mertens et al. |
| 2004/0259075 A1 | 12/2004 | Dimitrov et al. |
| 2005/0037000 A1 | 2/2005 | Stavenhagen et al. |
| 2005/0054832 A1 | 3/2005 | Lazar et al. |
| 2005/0064514 A1 | 3/2005 | Stavenhagen et al. |
| 2005/0100543 A1 | 5/2005 | Hansen et al. |
| 2005/0142539 A1 | 6/2005 | Herman |
| 2005/0215767 A1 | 9/2005 | Koenig et al. |
| 2005/0257285 A1 | 11/2005 | Gupta et al. |
| 2005/0260213 A1 | 11/2005 | Koenig et al. |
| 2006/0099216 A1 | 5/2006 | Nicholas Cardy et al. |
| 2006/0193849 A1 | 8/2006 | Krauss et al. |
| 2007/0004909 A1 | 1/2007 | Johnson et al. |
| 2007/0014795 A1 | 1/2007 | Dhodapkar et al. |
| 2007/0036799 A1 | 2/2007 | Stavenhagen et al. |
| 2007/0077246 A1 | 4/2007 | Koenig et al. |
| 2007/0135338 A1 | 6/2007 | O'Neil et al. |
| 2007/0140966 A1 | 6/2007 | Chang et al. |
| 2007/0274998 A1 | 11/2007 | Utku |
| 2008/0044417 A1 | 2/2008 | Johnson et al. |
| 2008/0044429 A1 | 2/2008 | Johnson et al. |
| 2008/0085277 A1 | 4/2008 | Cho et al. |
| 2008/0112961 A1 | 5/2008 | Stavenhagen et al. |
| 2008/0131435 A1 | 6/2008 | Stavenhagen et al. |
| 2008/0138344 A1 | 6/2008 | Stavenhagen et al. |
| 2008/0138349 A1 | 6/2008 | Stavenhagen et al. |
| 2008/0187517 A1 | 8/2008 | Herne |
| 2009/0017023 A1 | 1/2009 | Koenig et al. |
| 2009/0017026 A1 | 1/2009 | Koenig et al. |
| 2009/0017027 A1 | 1/2009 | Koenig et al. |
| 2009/0202537 A1 | 1/2009 | Johnson et al. |
| 2009/0053218 A1 | 2/2009 | Koenig et al. |
| 2009/0060910 A1 | 3/2009 | Johnson et al. |
| 2009/0074771 A1 | 3/2009 | Koenig et al. |
| 2009/0076251 A1 | 3/2009 | Koenig et al. |
| 2009/0092610 A1 | 4/2009 | Koenig et al. |
| 2009/0191195 A1 | 7/2009 | Tuaillon et al. |
| 2010/0174053 A1* | 7/2010 | Johnson ............... C07K 16/283 530/389.7 |
| 2010/0196362 A1 | 8/2010 | Stavenhagen et al. |
| 2010/0196372 A1 | 8/2010 | Johnson et al. |
| 2010/0254985 A1 | 10/2010 | Allan et al. |
| 2010/0322924 A1 | 12/2010 | Johnson et al. |
| 2011/0243941 A1 | 10/2011 | Stavenhagen et al. |
| 2011/0305714 A1 | 12/2011 | Stavenhagen et al. |
| 2012/0009186 A1 | 1/2012 | Koenig et al. |
| 2012/0141476 A1 | 6/2012 | Johnson et al. |
| 2012/0213781 A1 | 8/2012 | Hilbert |
| 2012/0219551 A1 | 8/2012 | Johnson et al. |
| 2012/0263711 A1 | 10/2012 | Stavenhagen et al. |
| 2012/0269811 A1 | 10/2012 | Johnson et al. |
| 2012/0276094 A1 | 11/2012 | Stavenhagen et al. |
| 2013/0295121 A1 | 11/2013 | Johnson et al. |

FOREIGN PATENT DOCUMENTS

| | | |
|---|---|---|
| JP | 2007-531788 | 10/2005 |
| WO | WO 1988/007089 | 9/1988 |
| WO | WO 1989/007142 | 8/1989 |
| WO | WO 1991/005548 | 5/1991 |
| WO | WO 1992/016562 | 10/1992 |
| WO | WO 1992/019244 | 11/1992 |
| WO | WO 1993/022332 | 11/1993 |
| WO | WO 1994/018330 | 8/1994 |
| WO | WO 1994/029351 | 12/1994 |
| WO | WO 1995/005468 | 2/1995 |
| WO | WO 1996/020698 | 7/1996 |
| WO | WO 1997/028267 | 8/1997 |
| WO | WO 1997/032572 | 9/1997 |
| WO | WO 1997/034631 | 9/1997 |
| WO | WO 1997/044013 | 11/1997 |
| WO | WO 1997/044362 | 11/1997 |
| WO | WO 1998/005787 | 2/1998 |
| WO | WO 1998/023289 | 6/1998 |
| WO | WO 1998/031346 | 7/1998 |
| WO | WO 1998/052975 | 11/1998 |
| WO | WO 1999/015154 | 4/1999 |
| WO | WO 1999/020253 | 4/1999 |
| WO | WO 1999/043713 | 9/1999 |
| WO | WO 1999/051642 | 10/1999 |
| WO | WO 1999/058572 | 11/1999 |
| WO | WO 1999/066903 | 12/1999 |
| WO | WO 2000/009560 | 2/2000 |
| WO | WO 2000/042072 | 7/2000 |
| WO | WO 2001/011059 | 2/2001 |
| WO | WO 2002/002781 | 1/2002 |
| WO | WO 2002/060919 | 8/2002 |
| WO | WO 2002/086070 | 10/2002 |
| WO | WO 2003/074679 | 9/2003 |
| WO | WO 2003/101485 | 12/2003 |
| WO | WO 2004/001064 | 12/2003 |
| WO | WO 2004/016750 | 2/2004 |
| WO | WO 2004/029207 | 4/2004 |

(56) References Cited

FOREIGN PATENT DOCUMENTS

| | | |
|---|---|---|
| WO | WO 2004/065423 | 8/2004 |
| WO | WO 2004/074455 | 9/2004 |
| WO | WO 2004/099249 | 11/2004 |
| WO | WO 2005/070963 | 8/2005 |
| WO | WO 2005/097202 | 10/2005 |
| WO | WO 2006/020114 | 2/2006 |
| WO | WO 2006/113665 | 10/2006 |
| WO | WO 2008/157379 | 12/2008 |
| WO | WO 2010/080538 | 7/2010 |
| WO | WO 2012/018687 | 2/2012 |
| WO | WO 2012/162067 | 11/2012 |
| WO | WO 2012/162068 | 11/2012 |
| WO | WO 2014/159940 | 10/2014 |
| WO | WO 2015/026892 | 2/2015 |

OTHER PUBLICATIONS

Alt et al., "Novel Tetravalent and Bispecific IgG-Like Antibody Molecules Combining Single-Chain Diabodies With the Immunoglobin Gamma 1 Fc or CH3 Region," FEBS Letters 454: 90-94, 1999.
Altman et al., "Phenotypic Analysis of Antigen-Specific T Lymphocytes", Science 274:94-96, 1996.
Angal et al., "A single amino acid substitution abolishes the heterogeneity of chimeric mouse-human (IgG4) antibody," Mol Immunol 30 :105-108, 1993.
Anonymous, "Boehringer Ingelheim and MacroGenics Announce Global Alliance to discover, Develop and Commercialize DART(tm)-Based Antibody Therapeutics;" Press Release of MacroGenics, Inc.; Oct. 26, 2010; 3 pages.
Anonymous, "MacroGenics Enters Global Research Collaboration and License Agreement with Pfizer;" Press Release of MacroGenics, Inc.; Oct. 26, 2010; 2 pages.
Apostolovic, B. et al. (2008) "pH-Sensitivity of the E3-K3 Heterodimeric Coiled Coil," Biomacromolecules 9:3173-3180.
Armour et al., "Differential binding to human FcgammaRIIa and FcgammaRIIb receptors by human IgG wildtype and mutant antibodies," Mol Immunol 40 :585-593, 2003.
Armour et al., "Recombinant human IgG molecules lacking Fcgamma receptor I binding and monocyte triggering activities," Eur J Immunol 29:2613-2624, 1999.
Armour et al., "The contrasting IgG-binding interactions of human and herpes simplex virus Fc receptors," Biochemical Society Transactions 30:495-500, 2002.
Armstrong, S. et al. "Heterogeneity of IgG1 monoclonal anti-Rh(D): an investigation using ADCC and macrophage binding assays," Brit. J. Haematol. 66:257-262 (1987).
Arndt, K.M. et al. (2001) "Helix-stabilized Fv (hsFv) Antibody Fragments: Substituting the Constant Domains of a Fab Fragment for a Heterodimeric Coiled-coil Domain," J. Molec. Biol. 312:221-228.
Arndt, K.M. et al. (2002) "Comparison of In Vivo Selection and Rational Design of Heterodimeric Coiled Coils," Structure 10:1235-1248.
Asano, R. et al. (2004) "A Diabody for Cancer Immunotherapy and its Functional Enhancement by Fusion of Human Fc Region," Abstract 3P-683, J. Biochem. 76(8):992.
Atwell et al. (1997) "Stable Heterodimers From Remodeling the Domain Interface of a Homodimer Using a Phage Display Library," J. Mol. Biol. 270: 26-35.
Baeuerle, P.A. et al. (2009) "Bispecific T-Cell Engaging Antibodies for Cancer Therapy," Cancer Res. 69(12):4941-4944.
Baggiolini M, Dewald B. "Cellular models for the detection and evaluation of drugs that modulate human phagocyte activity," Experientia. Oct. 15;44(10):841-848, 1988.
Bedzyk et al. (1989) "Comparison of Variable Region Primary Structures Within an Anti-Fluorescein Idiotype Family," J. Biol. Chem, 264(3):1565-1569.
Billadeau D.D. et al. (2002) "ITAMs Versus ITIMs: Striking a Balance During Cell Regulation," J. Clin. Invest. 2(109):161-1681.

Boder and Wittrup, "Optimal screening of surface-displayed polypeptide libraries," Biotechnol Prog 14:55-62, 1998.
Boder and Wittrup, "Yeast surface display for directed evolution of protein expression, affinity, and stability," Methods in Enzymology 328:430-444, 2000.
Boder and Wittrup, 1997, "Yeast surface display for screening combinatorial polypeptide libraries", Nature Biotechnology 15:553-557.
Boder et al., "Directed evolution of antibody fragments with monovalent femtomolar antigen-binding affinity," Proc. Natl. Acad. Sci. USA 97:10701-10705, 2000.
Boucher, C. et al. (2010) "Protein Detection by Western Blot Via Coiled-Coil Interactions," Analytical Biochemistry 399:138-140.
Bredius et al., "Role of neutrophil Fc gamma RIIa (CD32) and Fc gamma RIIIb (CD16) polymorphic forms in phagocytosis of human IgG1- and IgG3-opsonized bacteria and erythrocytes," Immunology 83:624-630, 1994.
Brekke et al., "Human IgG isotype-specific amino acid residues affecting complement-mediated cell lysis and phagocytosis.," Eur J Immunol 24:2542-2547, 1994.
Brown EJ., vol. 45 (Microbes as Tools for Cell Biology) in Methods in Cell Biololgy, Russell ed. Academic Press Inc. pp. 147-164, 1994.
Buchwald, et al. (1980) "Long-Term, Continuous Intravenous Heparin Administration by an Implantable Infusion Pump in Ambulatory Patients With Recurrent Venous Thrombosis," Surgery 88:507-516.
Burlmeister et al., "Crystal structure of the complex of rat neonatal Fc receptor with Fc," Nature 372:379-383, 1994.
Burton and Woof, "Human antibody effector function," Advances in Immunology 51:1-84, 1992.
Burton et al., "Molecular recognition of antibody (IgG) by cellular Fc receptor (FcRI)," Mol Immunol 25:1175-1181, 1988.
Burton, "Immunoglobulin G: functional sites," Mol Immunol 22:161-206, 1985.
Cachia, P.J. et al. (2004) "Synthetic Peptide Vaccine Development: Measurement of Polyclonal Antibody Affinity and Cross-Reactivity Using a New Peptide Capture and Release System for Surface Plasmon Resonance Spectroscopy," J. Mol. Recognit. 17:540-557.
Canfield and Morrison, "The binding affinity of human IgG for its high affinity Fc receptor is determined by multiple amino acids in the CH2 domain and is modulated by the hinge region," J Exp Med 173:1483-1491, 1991.
Cao et al. (2003) "Bispecific Antibody Conjugates in Therapeutics," Adv. Drug Deliv. Rev. 55:171-197.
Caron et al., "Engineered humanized dimeric forms of IgG are more effective antibodies," J Exp Med 176 :1191-5, 1992.
Carter et al., "Humanization of an anti-p185HER2 antibody for human cancer therapy," Proc. Natl. Acad. Sci. USA 89:4285-4289, 1992.
Cartron et al., "Therapeutic activity of humanized anti-CD20 monoclonal antibody and polymorphism in IgG Fc receptor FcgammaRIIIa gene," Blood 99 :754-758, 2002.
Chappel et al., "Identification of a secondary Fc gamma RI binding site within a genetically engineered human IgG antibody," J Biol. Chem 268:25124-25131, 1993.
Chappel et al., "Identification of the Fc gamma receptor class I binding site in human IgG through the use of recombinant IgG1-IgG2 hybrid and point-mutated antibodies," Proc. Natl. Acad. Sci USA 88:9036-9040, 1991.
Choi, B. et al. (2011) "Human B Cell Development and Antibody Production in Humanized NOD/SCID/IL-2Rγ(Null) (NSG) Mice Conditioned by Busulfan," J. Clin. Immunol. 31(2)253-264.
Chu, P. G. et al. (2001) "CD79: A Review," Appl. Immunohistochem. Molec. Morphol. 9(2):97-106.
Ciccimarra et al., "Localization of the IgG effector site for monocyte receptors," Proc. Natl. Acad. Sci. U.S.A. 72 :2081-2083, 1975.
Clynes and Ravetch, "Cytotoxic antibodies trigger inflammation through Fc receptors," Immunity 3:21-26, 1995.
Clynes et al., "Fc receptors are required in passive and active immunity to melanoma," Proc. Natl. Acad. Sci USA 95:652-656, 1998.
Clynes et al., "Inhibitory Fc receptors modulate in vivo cytoxicity against tumor targets," Nature Medicine 6 :443-446, 2000.

(56) References Cited

OTHER PUBLICATIONS

Clynes et al., "Modulation of immune complex-induced inflammation in vivo by the coordinate expression of activation and inhibitory Fc receptors," J Exp Med 189:179-185, 1999.
Clynes et al., "Uncoupling of immune complex formation and kidney damage in autoimmune glomerulonephritis," Science 279:1052-1054, 1998.
Cuesta, A.M. et al. (2010) "Multivalent Antibodies: When Design Surpasses Evolution," Trends in Biotechnol., 28(7):355-362.
De Crescenzo, G.D. et al. (2003) "Real-Time Monitoring of the Interactions of Two-Stranded de novo Designed Coiled-Coils: Effect of Chain Length on the Kinetic and Thermodynamic Constants of Binding," Biochemistry 42:1754-1763.
de Haas, Wien Kin "IgG-Fc receptors and the clinical relevance of their polymorphisms," Wien Klin Wochenscha 113:825-831, 2001.
de Kruif, J. et al. (1996) "Leucine Zipper Dimerized Bivalent and Bispecific scFv Antibodies from a Semi-synthetic Antibody Phage Display Library," J. Biol. Cherm. 271(13):7630-7634.
DeFranco, A.L. (1997) "The Complexity of Signaling Pathways Activated by the BCR," Curr. Opin. Immunol. 9:296-308.
Deisenhofer, "Crystallographic refinement and atomic models of a human Fc fragment and its complex with fragment B of protein A from *Staphylococcus aureus* at 2.9- and 2.8-A resolution," Biochem. 20:2361-2370, 1981.
Deo et al., "Clinical significance of IgG Fc receptors and Fc gamma R-directed immunotherapies," Immunology Today 18:127-135, 1997.
Duncan and Winter, "Localization of the binding site for the human high-affinity Fc receptor on IgG," Nature 332:563-564, 1988.
Duncan and Winter, "The binding site for C1q on IgG," Nature 332:738-740, 1988.
During et al. (1989) "Controlled Release of Dopamine From a Polymeric Brain Implant: In Vivo Characterization," Ann. Neurol. 25:351-356.
Dylke, J. et al. (2007) "Role of the extracellular and transmembrane domain of Ig-alpha/beta in assembly of the B cell antigen receptor (BCR)," Immunol. Lett. 112(1):47-57.
Edberg et al., "Modulation of Fcgamma and Complement Receptor Function by the Glycosyl-Phosphatidylinositol-Anchored Form of FcgammaRIII," Journal of Immunology 152: 5826-5835, 1994.
European Search Report EP 06750508 (2010) (19 pages).
European Search Report EP 08771050 (2010) (13 pages).
Fernandez-Rodriguez, J. et al. (2012) "Induced Heterodimerization and Purification of Two Target Proteins by a Synthetic Coiled-Coil Tag," Protein Sci. 21:511-519.
FitzGerald, et al., "Improved tumour targeting by disulphide stabilized diabodies expressed in Pichia pastoris," Protein Engineering 10(10): 1221-1225, 1997.
Flesch and Neppert, "Functions of the Fc receptors for immunoglobulin G," J Clin Lab Anal 14:141-156, 2000.
Gao, Y. et al. (2004) "Efficient Inhibition of Multidrug-Resistant Human Tumors With a Recombinant Bispecific Anti-P-Glycoprotein x Anti-CD3 Diabody," Leukemia 18(3):513-520.
Gauld, S.B. et al (2002) "B Cell Antigen Receptor Signaling: Roles in Cell Development and Disease," Science 296(5573):1641-1642.
Gelber J.S. et al. (2001) "Stimulatory and Inhibitory Signals Originating From the Macrophage Fcγ Receptors," Microbes and Infection, 3:131-139.
Gergeley et al., "Fc receptors on lymphocytes and K cells," Biochemical Society Transactions 12:739-743, 1984.
Gergely and Sarmay, "The two binding-site models of human IgG binding Fc gamma receptors," FASEB J 4:3275-3283, 1990.
Ghosh, T.S. et al. (2009) "End-To-End and End-To-Middle Interhelical Interactions: New Classes of Interacting Helix Pairs in Protein Structures," Acta Cryst. D65:1032-1041.
Greenwood and Clark, "Effector functions of matched sets of recombinant human IgG subclass antibodies". (final version edited Feb. 11, 1993).
Greenwood et al., "Engineering multiple-domain forms of the therapeutic antibody CAMPATH-1H: effects on complement lysis," Therapeutic Immunology 1:247-255, 1994.

Greenwood et al., "Structural motifs involved in human IgG antibody effector functions," Eur J Immunol 23:1098-1104, 1993.
Grigoryan, G. et al. (2008) "Structural Specificity in Coiled-Coil Interactions," Curr. Opin. Struc. Biol. 18:477-483.
Guo, J. et al. (2003) "[New Type Recombinant Antibody Fragment Scfv Multimer and Cancer Targeting]," Sheng Wu Yi Xue Gong Cheng Xue Za Zhi 20(2):361-365 (Abstract Only; Article in Chinese).
Guo, N. et al. (2005) "The Development of New Formats of Engineered Bispecific Antibodies," in Trends in Immunology Research, Veskler, Ed. Nova Science Publishers. Chapter 3:33-47.
Hadley et al., "The functional activity of Fc gamma RII and Fc gamma RIII on subsets of human lymphocytes," Immunology 76:446-451, 1992.
Hatta et al., "Association of Fc gamma receptor IIIB, but not of Fc gamma receptor IIA and IIIA polymorphisms with systemic lupus erythematosus in Japanese," Genes and Immunity 1:53-60, 1999.
Hayes, Fc Engineering to Enhance Monoclonal Antibody Effector Functions. (Presentation) Xecor, CA, 2003.
Herzenberg et al., "The history and future of the fluorescence activated cell sorter and flow cytometry: a view from Stanford," Clinical Chem. 2002:48:1819-1827, 2002.
Heyman, "Regulation of antibody responses via antibodies, complement, and Fc receptors," Annu Rev Immunol 18:709-737, 2000.
Hogarth et al., "Characterization of FcR Ig-binding sites and epitope mapping," Immunomethods 4 :17-24, 1994.
Holler et al., "In vitro evolution of a T cell receptor with high affinity for peptide-MHC," Proc. Natl. Acad. Sci. U.S.A. 97 :5387-92, 2000.
Holliger et al. (1993) "'Diabodies': Small Bivalent and Bispecific Antibody Fragments," Proc. Natl. Acad. Sci. (U.S.A.) 90:6444-6448.
Holliger et al. (1996) "Specific Killing of Lymphoma Cells by Cytotoxic T-Cells Mediated by a Bispecific Diabody," Protein Eng. 9:299-305.
Holliger et al. (1999) "Carcinoembryonic Antigen (CEA)-Specific T-cell Activation in Colon Carcinoma Induced by Anti-CD3 x Anti-CEA Bispecific Diabodies and B7 x Anti-CEA Bispecific Fusion Proteins," Cancer Res. 59:2909-2916.
Holliger et al., "Engineered antibody fragments and the rise of single domains," Nature Biotechnology 23(9): 1126-1135, Sep. 2005.
Howard et al. (1989) "Intracerebral Drug Delivery in Rats With Lesion-Induced Memory Deficits," J. Neurosurg. 7(1):105-112.
Hudson, P.J. et al. (1999) "High avi dity scFv multimers; diabodies and triabodies," J. Immunol. Methods 231(1-2):177-189.
Hulett et al., "Chimeric Fc receptors identify functional domains of the murine high affinity receptor for IgG," J Immunol 147 :1863-1868, 1991.
Hulett et al., "Identification of the IgG binding site of the human low affinity receptor for IgG Fc gamma RII. Enhancement and ablation of binding by site-directed mutagenesis," J. Biol. Chem 269:15287-15293, 1994.
Hulett et al., "Multiple regions of human Fc gamma RII (CD32) contribute to the binding of IgG," J. Biol. Chem. 270:21188-21194, 1995.
Idusogie et al., "Engineered antibodies with increased activity to recruit complement," J Immunol 166 :2571-2575, 2001.
Idusogie et al., "Mapping of the C1q binding site on rituxan, a chimeric antibody with a human IgG1 Fc," J Immunol 164: 4178-4184, 2000.
International Search Report and Written Opinion PCT/US2009/068577 (dated 2010) (14 pages).
International Search Report and Written Opinion PCT/US2011/045922 (dated 2011) (4 pages).
Isaacs et al., "A therapeutic human IgG4 monoclonal antibody that depletes target cells in humans," Clin Exp Immunol 106 :427-433, 1996.
Isaacs et al., "Therapy with monoclonal antibodies. An in vivo model for the assessment of therapeutic potential," J Immunol 148 :3062-3071, 1992.

(56) References Cited

OTHER PUBLICATIONS

Isaacs et al., "Therapy with monoclonal antibodies. II. The contribution of Fc gamma receptor binding and the influence of C(H)1 and C(H)3 domains on in vivo effector function," J Immunol 161 :3862-3869, 1998.
Jassal et al., "Remodeling glycans on IgG by genetic re-engineering," Biochem Soc Trans 26 :S113, 1998.
Jefferis and Lund, "Interaction sites on human IgG-Fc for FcgammaR: current models," Immunology Letters 82 :57-65, 2002.
Jefferis et al., "IgG-Fc-mediated effector functions: molecular definition of interaction sites for effector ligands and the role of glycosylation," Immunol Rev 163:59-76, 1998.
Jefferis et al., "Molecular definition of interaction sites on human IgG for Fc receptors (huFc gammaR)," Mol Immunol 27 :1237-1240, 1990.
Jefferis et al., "Recognition sites on human IgG for Fc gamma receptors: the role of glycosylation," Immunol Lett 44 :111-7, 1995.
Jendeberg et al., "Engineering of Fc(1) and Fc(3) from human immunoglobulin G to analyse subclass specificity for staphylococcal protein A," J Immunological Methods 201 :25-34, 1997.
Johansson, M.U. et al. (2002) "Structure, Specificity, and Mode of Interaction for Bacterial Albumin-Binding Modules," J. Biol. Chem. 277(10):8114-8120.
Johnson et al., (2010) "Effector Cell Recruitment with Novel Fv-based Dual-affinity Re-targeting Protein Leads to Potent Tumor Cytolysis and in Vivo B-cell Depletion," J. Mol. Biol (399) pp. 436-449.
Joliot et al. (1991) "Antennapedia Homeobox Peptide Regulates Neural Morphogenesis," Proc. Natl. Acad. Sci. (U.S.A.) 88:1864-1868.
Kadar et al., "Modulatory effect of synthetic human IgG Fc peptides on the in vitro immune response of murine spleen cells," Int J Immunpharmacol 13 :1147-55, 1991.
Kadar et al., "Synthetic peptides comprising defined sequences of CH-2 and CH-3 domains of human IgG1 induce prostaglandin E2 production from human peripheral blood mononuclear cells," Immunol Lett 32:59-63, 1992.
Kato et al., "Structural basis of the interaction between IgG and Fcγ receptors," J Mol Biol 295:213-224, 2000.
Keler et al., "Differential effect of cytokine treatment on Fc alpha receptor I- and Fc gamma receptor I-mediated tumor cytotoxicity by monocyte-derived macrophages," J. of Immunol. 164:5746-52, 2000.
Kieke et al., "Selection of functional T cell receptor mutants from a yeast surface-display library," Proc. Natl. Acad. Sci. U.S.A. 96 :5651-56, 1999.
Kim et al., "Analysis of FcγRIII and IgG Fc polymorphism reveals functional and evolutionary implications of protein-protein interaction," J Mol Evol 53:1-9, 2001.
Kim, K.M. et al. (1993) "Signalling Function of the B-Cell Antigen Receptors," Immun Rev. 132:125-146.
Klein et al., "Expression of biological effector functions by immunoglobulin G molecules lacking the hinge region," Proc. Natl. Acad. Sci. U.S.A. 78 :524-528, 1981.
Koene et al., "Fc gammaRIIIa-158V-F polymorphism influences the binding of IgG by natural killer cell Fc gammaRIIIa, independently of the Fc gammaRIIIa-48L-R-H phenotype," Blood 90 :1109-1114, 1997.
Kontermann, R.E. (2005) "Recombinant Bispecific Antibodies for Cancer Therapy," Acta. Pharmacol. Sin. 26(1):1-9.
Kortt, A.A. et al. (2001) "Dimeric and Trimeric Antibodies: High Avidity Scfvs for Cancer Targeting," Biomol. Eng. 18(3):95-108.
Kranz et al., "Mechanisms of ligand binding by monoclonal anti-fluorescyl antibodies," J. Biol. Chem. 257:6987-6995, 1982.
Kumpel, B.M. Brit. "Human monoclonal anti-D antibodies," J. Haematol. 71:415-420 (1989).
Langer (1990) "New Methods of Drug Delivery," Science 249:1527-1533.

Le Gall, F. et al. (Epub May 4, 2004) "Effect of Linker Sequences Between the Antibody Variable Domains on the Formation, Stability and Biological Activity of a Bispecific Tandem Diabody," Protein Eng Des Sel. 17(4):357-366.
Le, P.U. et al. (2009) "*Escherichia coli* Expression and Refolding of E-K-Coil-Tagged EGF Generates Fullybioactive EGF for Diverse Applications," Protein Expression and Purification 64:108-117.
Lehmann et al., "Phagocytosis: measurement by flow cytometry," J Immunol Methods. 243(1-2):229-42, 2000.
Lehrnbecher et al., "Variant genotypes of the low-affinity Fcgamma receptors in two control populations and a review of low-affinity Fcgamma receptor polymorphisms in control and disease populations," Blood 94:4220-4232, 1999.
Levy et al. (1985) "Inhibition of Calcification of Bioprosthetic Heart Valves by Local Controlled-Release Diphosphonate," Science 228:190-192.
Li et al., "Reconstitution of human Fc gamma RIII cell type specificity in transgenic mice," J Exp Med 183 :1259-1263, 1996.
Litowski, J.R. et al. (2002) "Designing Heterodimeric Two-Stranded α-Helical Coiled-Coils: The Effects of Hydrophobicity and α-Helical Propensity on Protein Folding, Stability, and Specificity," J. Biol. Chem. 277:37272-37279.
Liu et al., "Production of a mouse-human chimeric monoclonal antibody to CD20 with potent Fc-dependent biologic activity," J. Immunol. 139:3521-3526, 1987.
Lu, D. et al., (2003) "Di-diabody: a novel tetravalent bispecific antibody molecule by design," J. Immunol. Meth. 279:219-232.
Lu, D. et al., (2004) "The effect of variable domain orientation and arrangement on the antigen-binding activity of a recombinant human bispecific diabody," BBRC 318: 507-513.
Lu, et al., (2005) "A Fully Human Recombinant IgG-like Bispecific Antibody to Both the Epidermal Growth Factor Receptor and the Insulin-like Growth Factor Receptor for Enhanced Antitumor Activity," The Journal of Biological Chemistry, vol. 280(20) pp. 19665-19672.
Lund et al., "Expression and characterization of truncated forms of humanized L243 IgG1. Architectural features can influence synthesis of its oligosaccharide chains and affect superoxide production triggered through human Fcgamma receptor I," Eur J Biochem 267 :7246-57, 2000.
Lund et al., "Human Fc gamma RI and Fc gamma RII interact with distinct but overlapping sites on human IgG," J Immunol 147 :2657-62, 1991.
Lund et al., "Multiple binding sites on the CH2 domain of IgG for mouse Fc gamma R11," Molecular Immunology 29:53-59, 1992.
Lund et al., "Multiple interactions of IgG with its core oligosaccharide can modulate recognition by complement and human Fc gamma receptor I and influence the synthesis of its oligosaccharide chains," J Immunol 157 :4963-4969, 1996.
Lund et al., "Oligosaccharide-protein interactions in IgG can modulate recognition by Fc gamma receptors," FASEB J 9 :115-119, 1995.
Luo et al. (1995) "VL-Linker-VH Orientation-Dependent Expression of Single Chain Fv Containing an Engineered Disulfide-Stabilized Bond in the Framework Regions," J. Biochem. 4(118):825-831.
Maenaka et al., "The human low affinity Fcgamma receptors IIa, IIb, and III bind IgG with fast kinetics and distinct thermodynamic properties," J Biol Chem 48 :44898-904, 2001.
Mariuzza et al., (1987) "The Structural Basis of Antigen-Antibody Recognition," Annual Review of Biophysics and Biophysical Chemistry 16:139-159.
Marvin et al., "Recombinant approaches to IgG-like bispecific antibodies," Acta Pharmacologica Sinica, 26(6): 649-658, Jun. 2005
Mertens, N. et al., "New Recombinant Bi- and Trispecific Antibody Derivatives," In: Novel Frontiers in the Production of Compounds for Biomedical Use, vol. 1; van Broekhoven, A. et al. (Eds.); Kluwer Academic Publishers, Dordrecht, The Netherlands.
Michaelsen et al., "One disulfide bond in front of the second heavy chain constant region is necessary and sufficient for effector functions of human IgG3 without a genetic hinge," Immunolgy 91 :9243-9247, 1994.

(56) References Cited

OTHER PUBLICATIONS

Moore, P.A. et al., (2011) "Application of Dual Affinity Retargeting Molecules to Achieve Optimal Redirected T-Cell Killing of B-Cell Lymphoma," Blood 117:4542-4551.
Morgan et al., "The N-terminal end of the CH2 domain of chimeric human IgG1 anti-HLA-DR is necessary for C1q, Fc gamma RI and Fc gamma RIII binding," Immunology 86 :319-324, 1995.
Morrison et al., "Structural determinants of IgG structure," Immunologist 2 :119-124, 1994.
Munn et al., "Phagocytosis of tumor cells by human monocytes cultured in recombinant macrophage colony-stimulating factor," J Exp Med. 172(1):231-7, 1990.
Nagarajan et al., "Ligand binding and phagocytosis by CD16 (Fc gamma receptor III) isoforms. Phagocytic signaling by associated zeta and gamma subunits in Chinese hamster ovary cells," J Biol Chem 270 :25762-25770, 1995.
Nakamura, T. et al. (1992) "Heterogeneity of Immunoglobulin-Associated Molecules on Human B Cells Identified by Monoclonal Antibodies," Proc. Natl. Acad. Sci. (USA) 89:8522-8526).
Neuberger et al., "Recombinant antibodies possessing novel effector functions," Nature 312 :604-608, 1984.
Ning et al. (1996) "Intratumoral Radioimmunothempy of a Human Colon Cancer Xenograft Using a Sustained-Release Gel," Radiotherapy & Oncology 39:179-189.
Norderhaug et al., "Chimeric mouse human IgG3 antibodies with an IgG4-like hinge region induce complement-mediated lysis more efficiently than IgG3 with normal hinge," Eur J Immunol 21:2379-84, 1991.
Nose and Leanderson, "Substitution of asparagine324 with aspartic acid in the Fc portion of mouse antibodies reduces their capacity for C1q binding," Eur J Immunol 19 :2179-81, 1989.
Okazaki et al., "Fucose depletion from human IgG1 oligosaccharide enhances binding enthalpy and association rate between IgG1 and FcgammaRIIIa," J Mol Biol 336 :1239-1249, 2004.
Olafsen et al., "Covalent disulfide-linked anti-CEA diabody allows site-specific conjugation and radiolabeling for tumor targeting applications," Protein Engineering, Design & Selection, 17(1): 21-27, 2004.
Orfao and Ruiz-Arguelles, "General concepts about cell sorting techniques," Clinical Biochem. 29:5-9, 1996.
Pack, P. et al. (1992) "Miniantibodies: Use of Amphipathic Helices to Produce Functional, Flexibly Linked Dimeric Fv Fragments with High Avidity in *Escherichia coli*," 31(6):1579-1584.
Partridge et al., "The use of anti-IgG monoclonal antibodies in mapping the monocyte receptor site on IgG," Mol Immunol. 23(12):1365-72, 1986.
Perri, R. et al. (2007) "Graft Vs. Host Disease After Liver Transplantation: A New Approach is Needed," Liver Transpl. 13:1092-1099.
Perussia "Human Natural Killer Cell Protocols" in Methods Molecular Biology. vol. 121 (Campbell et al. eds.) Humana Press Inc., Totowa, NJ. 179-92, 2000.
Pollack, M.S. et al. (2005) "Severe, Late-Onset Graft-Versus-Host Disease in a Liver Transplant Recipient Documented by Chimerism Analysis," Hum. Immunol. 66:28-31.
Radaev and Sun, "Recognition of immunoglobulins by Fcgamma receptors," Molecular Immunology 38 :1073-1083, 2001.
Rankin et al. "CD32B, The Human Inhibitory Fc-γ Receptor IIB, As a Target for Monoclonal Antibody Therapy of B-Cell Lymphoma," (2006) Blood 108(7):2384-2391.
Ravetch (1994) "Fc Receptors: Rubor Redux," Cell 78:553-560.
Ravetch and Bolland, "IgG Fc receptors," Annu Rev Immunol 19:275-90, 2001.
Ravetch and Clynes, "Divergent roles for Fc receptors and complement in vivo," Annu Rev Immunol 16:421-432, 1998.
Ravetch and Kinet, "Fc receptors," Annu Rev Immunol 9:457-492, 1991.
Ravetech and Lanier, "Immune inhibitory receptors," Science 290:84-89, 2000.

Redpath et al., "The influence of the hinge region length in binding of human IgG to human Fcgamma receptors," Hum Immunol 59 :720-727, 1998.
Reff et al., "Depletion of B cells in vivo by a chimeric mouse human monoclonal antibody to CD20," Blood 83:435-445, 1994.
Ridgway et al. (1996) 'Knobs-Into-Holes' Engineering of Antibody CH3 Domains for Heavy Chain Heterodimerization, Protein Engr. 9:617-621.
Riechmann et al., "Reshaping human antibodies for therapy," Nature. 332(6162):323-7, 1988.
Rothlisberger, D. et al. (2005) "Domain Interactions in the Fab Fragment: A Comparative Evaluation of the Single-chain Fv and Fab Format Engineered with Variable Domains of Different Stability," J. Molec. Biol. 347:773-789.
Sanchez, P.V. et al. (2009) "A Robust Xenotransplantation and Allograft Rejection," Transplantation 89(5):527-536.
Sarmay et al., "Ligand inhibition studies on the role of Fc receptors in antibody-dependent cell-mediated cytotoxicity," Mol Immunol 21 :43-51, 1984.
Sarmay et al., "Mapping and comparison of the interaction sites on the Fc region of IgG responsible for triggering antibody dependent cellular cytotoxicity (ADCC) through different types of human Fc gamma receptor," Mol Immunol 29 :633-639, 1992.
Sarmay et al., "The effect of synthetic peptides corresponding to Fc sequences in human IgG1 on various steps in the B cell activation pathway," Eur J Immunol 18 :289-294, 1988.
Sartelet, H. et al.(2012) "Description of a New Xenograft Model of Metastatic Neuroblastoma Using NOD/SCID/Il2rg Null (NSG) Mice," In Vivo 26(1):19-29.
Saudek et al. (1989) "A Preliminary Trial of the Programmable Implantable Medication System for Insulin Delivery," N. Engl. J. Med. 321:574-579.
Sautes-Fridman et al., "Fc gamma receptors: a magic link with the outside world," ASHI Quarterley, $4^{th}$ Quarter:148-151, 2003.
Schaffner et al., "Chimeric interleukin 2 receptor alpha chain antibody derivatives with fused mu and gamma chains permit improved recruitment of effector functions," Mol Immunol 32 :9-20, 1995 (Erratum in 32 :1299, 1995).
Schatz et al., "Use of peptide libraries to map the substrate specificity of a peptide-modifying enzyme: a 13 residue consensus peptide specifies biotinylation in *Escherichia coli*," Bio-Technology 11:1138-1143, 2000.
Sensel et al., "Amino acid differences in the N-terminus of C(H)2 influence the relative abilities of IgG2 and IgG3 to activate complement," Molecular Immunology 34:1019-1029, 1997.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276 :6591-6604, 2001.
Shopes et al., "Recombinant human IgG1-murine IgE chimeric Ig. Construction, expression, and binding to human Fc gamma receptors," J Immunol 145 :3842-3848, 1990.
Shopes, "A genetically engineered human IgG mutant with enhanced cytolytic activity," J Immunol 148 :2918-2922, 1992.
Shopes, "A genetically engineered human IgG with limited flexibility fully initiates cytolysis via complement," Molecular Immunology 30 :603-609, 1993.
Shusta et al., "Directed evolution of a stable scaffold for T-cell receptor engineering," Nature Biotechnology 18:754-759, 2000.
Shusta et al., "Increasing the secretory capacity of *Saccharomyces cerevisiae* for production of single-chain antibody fragments," Nature Biotechnology 16:773-777, 1998.
Shusta et al., "Yeast polypeptide fusion surface display levels predict thermal stability and soluble secretion efficiency," J Mol Biol 292:949-956, 1999.
Smith and Morrison, "Recombinant polymeric IgG: an approach to engineering more potent antibodies," Bio-Technology 12:683-688, 1994.
Sondermann and Oosthuizen, "The structure of Fc receptor-Ig complexes: considerations on stoichiometry and potential inhibitors," Immunology Letters, 82:51-56, 2002.

(56) References Cited

OTHER PUBLICATIONS

Sondermann et al., "Crystal structure of the soluble form of the human fcgamma-receptor IIb: a new member of the immunoglobulin superfamily at 1.7 A resolution," EMBO J 18:1095-1103, 1999.
Sondermann et al., "Molecular basis for immune complex recognition: a comparison of Fc-receptor structures," J. Mol. Biol. 309:737-749, 2001.
Sondermann et al., "The 3.2-A crystal structure of the human IgG1 Fc fragment-Fc gammaRIII complex," Nature 406:267-273, 2000.
Song et al. (1995) "Antibody Mediated Lung Targeting of Long-Circulating Emulsions," PDA Journal of Pharmaceutical Science & Technology 50:372-397.
Spranger, S. et al. (2012) "NOD/scid IL-2Rg(null) Mice: A Preclinical Model System to Evaluate Human Dendritic Cell-Based Vaccine Strategies in vivo," J. Transl. Med. 10:30.
Staerz et al. (1985) "Hybrid Antibodies Can Target Sites for Attack by T Cells," Nature 314:628-631.
Steinkruger, J.D. et al. (2012) "The d'-d-d' Vertical Triad is Less Discriminating Than the a'-a-a' Vertical Triad in the Antiparallel Coiled-coil Dimer Motif," J. Amer. Chem. Soc. 134(5):2626-2633.
Steplewski et al., "Biological activity of human-mouse IgG1, IgG2, IgG3, and IgG4 chimeric monoclonal antibodies with antitumor specificity," Proc. Natl. Acad. Sci. U.S.A. 85:4852-4856, 1988.
Stork, R. et al. (2007) "A Novel Tri-Functional Antibody Fusion Protein With Improved Pharmacokinetic Properties Generated by Fusing a Bispecific Single-Chain Diabody With an Albumin-Binding Domain From Streptococcal Protein G," Protein Engineering, Design & Selection 20(11):569-576.
Straussman, R. et al. (2007) "Kinking the Coiled Coil—Negatively Charged Residues at the Coiled-coil Interface," J. Molec. Biol. 366:1232-1242.
Strohmeier et al., "Role of the Fc gamma R subclasses Fc gamma RII and Fc gamma RIII in the activation of human neutrophils by low and high valency immune complexes," J Leukocyte Biol 58:415-422, 1995.
Sudhindran, S. et al. (2003) "Treatment of Graft-Versus-Host Disease After Transplantation With Basiliximab Followed by Bowel Resection," Am J Transplant. 3:1024-1029.
Sylvestre and Ravetch, "A dominant role for mast cell Fc receptors in the Arthus reaction," Immunity 5:387-390, 1996.
Sylvestre and Ravetch, "Fc receptors initiate the Arthus reaction: redefining the inflammatory cascade," Science 265:1095-1098, 1994.
Takai et al., "Augmented humoral and anaphylactic responses in Fc gamma RII-deficient mice," Nature 379:346-349, 1996.
Takai et al., "FcR gamma chain deletion results in pleiotrophic effector cell defects," Cell 76 :519-529, 1994.
Takai, "Roles of Fc receptors in autoimmunity," Nature Reviews 2:580-592, 2002.
Takemura, S. et al. (2000) "Construction of a Diabody (Small Recombinant Bispecific Antibody) Using a Refolding System," Protein Eng. 13(8):583-588.
Tamm et al., "The IgG binding site of human FcγRIIIB receptor involves CC' and FG loops of the membrane-proximal domain," J Biol Chem 271:3659-3666, 1996.
Tao et al., "Structural features of human immunoglobulin G that determine isotype-specific differences in complement activation," J Exp Med 178:661-667, 1993.
Tao et al., "The differential ability of human IgG1 and IgG4 to activate complement is determined by the COOH-terminal sequence of the CH2 domain," J Exp Med 173:1025-1028, 1991.
Todorovska, A. et al. (2001) "Design and Application of Diabodies, Triabodies and Tetrabodies for Cancer Targeting," J. Immunol. Methods 248(1-2):47-66.
Trindandapani et al. (2002) "Regulated Expression and Inhibitory Function of FcgammaRIIB in Human Monocytic Cells," J. Biol. Chem. 277(7):5082-5089.
Tripet, B. et al. (2002) "Kinetic Analysis of the Interactions between Troponin C and the C-terminal Troponin I Regulatory Region and Validation of a New Peptide Delivery-Capture System used for Surface Plasmon Resonance," J. Molec. Biol. 323:345-362.

Unkeless, J.C. et al. (1995) "Function of Human Fc Gamma RIIA and Fc Gamma RIIIB," Semin. Immunol. 7(1):37-44.
Van Sorge et al., "FcgammaR polymorphisms: Implications for function, disease susceptibility and immunotherapy," Tissue Antigens 61:189-202, 2003.
VanAntwerp and Wittrup, "Fine affinity discrimination by yeast surface display and flow cytometry," Biotechnol Prog 16:31-37, 2000.
Veri et al. (Epub Mar. 26, 2007) "Monoclonal antibodies capable of discriminating the human inhibitory Fcgamma-receptor IIB (CD32B) from the activating Fcgamma-receptor IIA (CD32A): biochemical, biological and functional characterization," Immunology 121(3):392-404.
Veri, et al. (Jul. 2010) "Therapeutic Control of B Cell Activation via Recruitment of Fcγ Receptor IIb (CD32B) Inhibitory Function With a Novel Bispecific Antibody Scaffold," Arthritis & Rheumatism, vol. 62(7): 1933-1943.
Vidarte, "Serine 132 is the C3 covalent attachment point on the CH1 domain of human IgG1," J Biol Chem 276:38217-38233, 2001.
Von Bonin, M. et al. (2013) "in Vivo Expansion of Co-Transplanted T Cells Impacts on Tumor Re-Initiating Activity of Human Acute Myeloid Leukemia in NSG Mice," PLoS One. 8(4):e60680.
Ward and Ghetie, "The effector functions of immunoglobulins: implications for therapy," Therapeutic Immunology 2:77-94, 1995.
Weng and Levy, "Two immunoglobulin G fragment C receptor polymorphisms independently predict response to rituximab in patients with follicular lymphoma," J Clin Oncol 21:3940-3947, 2003.
Wiener, E. et al. "Differences between the activities of human monoclonal IgG1 and IgG3 anti-D antibodies of the Rh blood group system in their abilities to mediate effector functions of monocytes," Immunol. 65:159-163 (1988).
Wing et al., "Mechanism of first-dose cytokine-release syndrome by CAMPATH 1-H: Involvement ofCD16 (FcγRIII) and CD11a-CD18 (LFA-1) on NK cells," J Clin Invest 98 :2819-2826, 1996.
Wingren et al., "Comparison of surface properties of human IgA, IgE, IgG and IgM antibodies with identical and different specificities," Scand J Immunol 44:430-436, 1996.
Wittrup, "The single cell as a microplate well," Nat Biotechnol 18:1039-1040, 2000.
Wittrup, "Protein engineering by cell-surface display," Curr, Opin. Biotechnol. 12:395-399, 2001.
Woof et al., "Localisation of the monocyte-binding region on human immunoglobulin G," Mol Immunol 23 :319-330, 1986.
Woolfson, D.N. (2005) "The Design of Coiled-Coil Structures and Assemblies," Adv. Prot. Chem. 70:79-112.
Wu et al., (1987) "Receptor-Mediated In Vitro Gene Transformation by a Soluble DNA Carrier System," J. Biol. Chemi. 262:4429-4432.
Wu et al., "A novel polymorphism of FcγRIIIa (CD16) alters receptor function and predisposes to autoimmune disease," J Clin Invst 100 :1059-1070, 1997.
Wu et al., "Multimerization of a chimeric anti-CD20 single-chain Fv-Fc fusion protein is mediated through variable domain exchange," Protein Engineering 14(2): 1025-1033 (2001).
Wu, A.M et al. (1999) "Designer Genes: Recombinant Antibody Fragments for Biological Imaging," Q. J. Nucl. Med. 44(3):268-283.
Xie et al., (2005) "A New Format of Bispecific Antibody: Highly Efficient Heterodimerization, Expression and Tumor Cell Lysis," J. Immunol. Methods 296:95-101.
Xiong, D. et al. (2002) "Efficient Inhibition of Human B-Cell Lymphoma Xenografts With an Anti-CD20 x Anti-CD3 Bispecific Diabody," Cancer Lett. (2002) 177(1):29-39.
Xu et al., "Residue at position 331 in the IgG1 and IgG4 CH2 domains contributes to their differential ability to bind and activate complement," J Biol Chem 269 :3469-3474, 1994.
Yeung and Wittrup, "Quantitative screening of yeast surface-displayed polypeptide libraries by magnetic bead capture," Biotechnol Prog 18:212-220, 2002.
Zeidler et al., "The Fc-region of a new class of intact bispecific antibody mediates activation of accessory cells and NK cells and induces direct phagocytosis of tumour cells," British J Cancer 83:261-266, 2000.

(56) References Cited

OTHER PUBLICATIONS

Zeng, Y. et al. (2008) "A Ligand-Pseudoreceptor System Based on de novo Designed Peptides for the Generation of Adenoviral Vectors With Altered Tropism," J. Gene Med. 10:355-367.
Zhu, Z. et al.(1997) "Remodeling Domain Interfaces to Enhance Heterodimer Formation," Protein Sci. 6:781-788.
Zuckier et al., "Chimeric human-mouse IgG antibodies with shuffled constant region exons demonstrate that multiple domains contribute to in vivo half-life," Cancer Res 58 :3905-3908, 1998.
Zuo et al. (2000) "An Efficient Route to the Production of an IgG-Like Bispecific Antibody," Protein Engineering 13(5):361-367.
International Search Report PCT/US2014/049848 (WO 2015/021089) (dated Dec. 22, 2014) (4 Pages).
Mawad, R. et al. (2009) "Graft-Versus-Host Disease Presenting With Pancytopenia After En Bloc Multiorgan Transplantation: Case Report and Literature Review," Transplant Proc. 41:4431-4433.
DePaoli, A.M. et al. (1992) "Graft-Versus-Host Disease and Liver Transplantation," Ann. Intern. Med. 117:170-171.
Cambier, J.C. (1995) "New Nomenclature for the Reth Motif (or ARH1/TAM/ARAM/YXXL)," Immunol. Today 16:110.
Burton et al. (1992) "*Human Antibody Effector Function*," Advances in Immunology 51:1-64.
Johnson et al. (2010) "*Effector Cell Recruitment with Novel Fv-based Dual-affinity Re-targeting Protein Leads to Potent Tumor Cytolysis and in Vivo B-cell Depletion*," J. Mol. Biol (399):436-449.

\* cited by examiner

- - - - GAH IgM μ (anti-μ): 30 μg/ml
——— + CD32B x CD79B non-Fc Diabody
- - - - + CD32B x CD79B (ABD) non-Fc Diabody
——— + CD32B x CD79B Fc Diabody

SEQUENCE LISTING

```
<160> NUMBER OF SEQ ID NOS: 25

<210> SEQ ID NO 1
<211> LENGTH: 10
<212> TYPE: PRT
<213> ORGANISM: Homo sapiens

<400> SEQUENCE: 1

Asp Lys Thr His Thr Cys Pro Pro Cys Pro
1               5                   10

<210> SEQ ID NO 2
<211> LENGTH: 5
<212> TYPE: PRT
<213> ORGANISM: Homo sapiens

<400> SEQUENCE: 2

Ala Pro Ser Ser Ser
1               5

<210> SEQ ID NO 3
<211> LENGTH: 8
<212> TYPE: PRT
<213> ORGANISM: Homo sapiens
```

```
<400> SEQUENCE: 3

Ala Pro Ser Ser Ser Pro Met Glu
1               5

<210> SEQ ID NO 4
<211> LENGTH: 8
<212> TYPE: PRT
<213> ORGANISM: Artificial Sequence
<220> FEATURE:
<223> OTHER INFORMATION: Linker 2

<400> SEQUENCE: 4

Gly Gly Gly Ser Gly Gly Gly Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Linker 3

<400> SEQUENCE: 5

Gly Gly Cys Gly Gly Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Linker 4

<400> SEQUENCE: 6

Gly Gly Gly Asn Ser
1               5

<210> SEQ ID NO 7
<211> LENGTH: 28
<212> TYPE: PRT
<213> ORGANISM: Artificial Sequence
<220> FEATURE:
<223> OTHER INFORMATION: Heterodimer-Promoting E-Coil Domain

<400> SEQUENCE: 7

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 8
<211> LENGTH: 28
<212> TYPE: PRT
<213> ORGANISM: Artificial Sequence
<220> FEATURE:
<223> OTHER INFORMATION: Heterodimer-Promoting K-Coil Doamin

<400> SEQUENCE: 8

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 9
<211> LENGTH: 217
```

```
<212> TYPE: PRT
<213> ORGANISM: Artificial Sequence
<220> FEATURE:
<223> OTHER INFORMATION: Preferred Sequence For The CH2 And CH3 Domains
      Of An Antibody Fc Region Present In The First Polypeptide Chain

<400> SEQUENCE: 9

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
            210                 215

<210> SEQ ID NO 10
<211> LENGTH: 217
<212> TYPE: PRT
<213> ORGANISM: Artificial Sequence
<220> FEATURE:
<223> OTHER INFORMATION: Preferred Sequence For The CH2 And CH3 Domains
      Of An Antibody Fc Region Present In The Third Polypeptide Chain

<400> SEQUENCE: 10

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Lys
        210                 215
```

<210> SEQ ID NO 11
<211> LENGTH: 107
<212> TYPE: PRT
<213> ORGANISM: Artificial Sequence
<220> FEATURE:
<223> OTHER INFORMATION: Preferred Sequence for the VL Domain of an Antibody that Binds CD32B

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Lys Ala Pro Arg Arg Leu Ile
        35                  40                  45

Tyr Ala Ala Ser Thr Leu Asp Ser Gly Val Pro Ser Arg Phe Ser Gly
    50                  55                  60

Ser Glu Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Phe Ser Tyr Pro Leu
                85                  90                  95

Thr Phe Gly Gly Gly Thr Lys Val Glu Ile Lys
            100                 105
```

<210> SEQ ID NO 12
<211> LENGTH: 116
<212> TYPE: PRT
<213> ORGANISM: Artificial Sequence
<220> FEATURE:
<223> OTHER INFORMATION: Preferred Sequence for the VH Domain of an Antibody that Binds CD32B

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Asn Lys Ala Lys Asn His Ala Thr Tyr Tyr Ala Glu
    50                  55                  60
```

```
Ser Val Ile Gly Arg Phe Thr Ile Ser Arg Asp Asp Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Gly Ala Leu Gly Leu Asp Tyr Trp Gly Gln Gly Thr Leu Val
            100                 105                 110

Thr Val Ser Ser
            115

<210> SEQ ID NO 13
<211> LENGTH: 112
<212> TYPE: PRT
<213> ORGANISM: Artificial Sequence
<220> FEATURE:
<223> OTHER INFORMATION: Preferred Sequence for the VL Domain of an
      Antibody that Binds CD79b

<400> SEQUENCE: 13

Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asp Ser
                 20                  25                  30

Asp Gly Lys Thr Tyr Leu Asn Trp Phe Gln Gln Arg Pro Gly Gln Ser
             35                  40                  45

Pro Asn Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Leu Thr Phe Gly Gly Gly Thr Lys Leu Glu Ile Lys
            100                 105                 110

<210> SEQ ID NO 14
<211> LENGTH: 113
<212> TYPE: PRT
<213> ORGANISM: Artificial Sequence
<220> FEATURE:
<223> OTHER INFORMATION: Preferred Sequence for the VH Domain of an
      Antibody that Binds CD79b

<400> SEQUENCE: 14

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Trp Met Asn Trp Val Arg Gln Ala Pro Gly Gln Gly Leu Glu Trp Ile
             35                  40                  45

Gly Met Ile Asp Pro Ser Asp Ser Glu Thr His Tyr Asn Gln Lys Phe
 50                  55                  60

Lys Asp Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ala Met Gly Tyr Trp Gly Gln Gly Thr Thr Val Thr Val Ser
            100                 105                 110

Ser
```

<210> SEQ ID NO 15
<211> LENGTH: 502
<212> TYPE: PRT
<213> ORGANISM: Artificial Sequence
<220> FEATURE:
<223> OTHER INFORMATION: Preferred Sequence for the First Polypeptide Chain

<400> SEQUENCE: 15

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ala Pro Ser Ser Ser Pro Met Glu Asp Ile Gln Met Thr
225                 230                 235                 240

Gln Ser Pro Ser Ser Leu Ser Ala Ser Val Gly Asp Arg Val Thr Ile
                245                 250                 255

Thr Cys Arg Ala Ser Gln Glu Ile Ser Gly Tyr Leu Ser Trp Leu Gln
            260                 265                 270

Gln Lys Pro Gly Lys Ala Pro Arg Arg Leu Ile Tyr Ala Ala Ser Thr
        275                 280                 285

Leu Asp Ser Gly Val Pro Ser Arg Phe Ser Gly Ser Glu Ser Gly Thr
    290                 295                 300

Glu Phe Thr Leu Thr Ile Ser Ser Leu Gln Pro Glu Asp Phe Ala Thr
305                 310                 315                 320

Tyr Tyr Cys Leu Gln Tyr Phe Ser Tyr Pro Leu Thr Phe Gly Gly Gly
                325                 330                 335

Thr Lys Val Glu Ile Lys Gly Gly Ser Gly Gly Gly Gly Gln Val
            340                 345                 350

Gln Leu Val Gln Ser Gly Ala Glu Val Lys Lys Pro Gly Ala Ser Val
        355                 360                 365
```

```
Lys Val Ser Cys Lys Ala Ser Gly Tyr Thr Phe Thr Ser Tyr Trp Met
    370                 375                 380

Asn Trp Val Arg Gln Ala Pro Gly Gln Gly Leu Glu Trp Ile Gly Met
385                 390                 395                 400

Ile Asp Pro Ser Asp Ser Glu Thr His Tyr Asn Gln Lys Phe Lys Asp
                405                 410                 415

Arg Val Thr Met Thr Thr Asp Thr Ser Thr Ser Thr Ala Tyr Met Glu
                420                 425                 430

Leu Arg Ser Leu Arg Ser Asp Asp Thr Ala Val Tyr Tyr Cys Ala Arg
                435                 440                 445

Ala Met Gly Tyr Trp Gly Gln Gly Thr Thr Val Thr Val Ser Ser Gly
    450                 455                 460

Gly Cys Gly Gly Gly Glu Val Ala Ala Leu Glu Lys Glu Val Ala Ala
465                 470                 475                 480

Leu Glu Lys Glu Val Ala Ala Leu Glu Lys Glu Val Ala Ala Leu Glu
                485                 490                 495

Lys Gly Gly Gly Asn Ser
                500

<210> SEQ ID NO 16
<211> LENGTH: 270
<212> TYPE: PRT
<213> ORGANISM: Artificial Sequence
<220> FEATURE:
<223> OTHER INFORMATION: Preferred Sequence for the Second Polypeptide
      Chain

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Asn Arg Leu Ile Tyr Leu Val Ser Lys Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Leu Thr Phe Gly Gly Gly Thr Lys Leu Glu Ile Lys
            100                 105                 110

Gly Gly Gly Ser Gly Gly Gly Gly Glu Val Gln Leu Val Glu Ser Gly
        115                 120                 125

Gly Gly Leu Val Gln Pro Gly Gly Ser Leu Arg Leu Ser Cys Ala Ala
    130                 135                 140

Ser Gly Phe Thr Phe Ser Asp Ala Trp Met Asp Trp Val Arg Gln Ala
145                 150                 155                 160

Pro Gly Lys Gly Leu Glu Trp Val Ala Glu Ile Arg Asn Lys Ala Lys
                165                 170                 175

Asn His Ala Thr Tyr Tyr Ala Glu Ser Val Ile Gly Arg Phe Thr Ile
            180                 185                 190

Ser Arg Asp Asp Ala Lys Asn Ser Leu Tyr Leu Gln Met Asn Ser Leu
        195                 200                 205

Arg Ala Glu Asp Thr Ala Val Tyr Tyr Cys Gly Ala Leu Gly Leu Asp
    210                 215                 220
```

```
Tyr Trp Gly Gln Gly Thr Leu Val Thr Val Ser Ser Gly Gly Cys Gly
225                 230                 235                 240

Gly Gly Lys Val Ala Ala Leu Lys Glu Lys Val Ala Ala Leu Lys Glu
            245                 250                 255

Lys Val Ala Ala Leu Lys Glu Lys Val Ala Ala Leu Lys Glu
            260                 265                 270

<210> SEQ ID NO 17
<211> LENGTH: 227
<212> TYPE: PRT
<213> ORGANISM: Artificial Sequence
<220> FEATURE:
<223> OTHER INFORMATION: Preferred Sequence for the Third Polypeptide
      Chain

<400> SEQUENCE: 17

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Lys
225

<210> SEQ ID NO 18
<211> LENGTH: 4
<212> TYPE: PRT
<213> ORGANISM: Artificial Sequence
<220> FEATURE:
<223> OTHER INFORMATION: Linker 5

<400> SEQUENCE: 18

Gly Gly Gly Ser
1
```

<210> SEQ ID NO 19
<211> LENGTH: 46
<212> TYPE: PRT
<213> ORGANISM: Artificial Sequence
<220> FEATURE:
<223> OTHER INFORMATION: Preferred Albumin-Binding Domain (ABD)

<400> SEQUENCE: 19

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 20
<211> LENGTH: 312
<212> TYPE: PRT
<213> ORGANISM: Artificial Sequence
<220> FEATURE:
<223> OTHER INFORMATION: Amino Acid Sequence of First Polypeptide Chain
      of CD32B x CD79b (ABD) Diabody

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Lys Ala Pro Arg Arg Leu Ile
        35                  40                  45

Tyr Ala Ala Ser Thr Leu Asp Ser Gly Val Pro Ser Arg Phe Ser Gly
    50                  55                  60

Ser Glu Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Phe Ser Tyr Pro Leu
                85                  90                  95

Thr Phe Gly Gly Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Met Asn Trp Val Arg Gln Ala Pro Gly Gln Gly Leu
145                 150                 155                 160

Glu Trp Ile Gly Met Ile Asp Pro Ser Asp Ser Glu Thr His Tyr Asn
                165                 170                 175

Gln Lys Phe Lys Asp Arg Val Thr Met Thr Thr Asp Thr Ser Thr Ser
            180                 185                 190

Thr Ala Tyr Met Glu Leu Arg Ser Leu Arg Ser Asp Asp Thr Ala Val
        195                 200                 205

Tyr Tyr Cys Ala Arg Ala Met Gly Tyr Trp Gly Gln Gly Thr Thr Val
    210                 215                 220

Thr Val Ser Ser Gly Gly Cys Gly Gly Gly Glu Val Ala Ala Leu Glu
225                 230                 235                 240

Lys Glu Val Ala Ala Leu Glu Lys Glu Val Ala Ala Leu Glu Lys Glu
                245                 250                 255

Val Ala Ala Leu Glu Lys Gly Gly Gly Ser Leu Ala Glu Ala Lys Val 260                 265                 270
Leu Ala Asn Arg Glu Leu Asp Lys Tyr Gly Val Ser Asp Tyr Tyr Lys
                275                 280                 285

Asn Leu Ile Asp Asn Ala Lys Ser Ala Glu Gly Val Lys Ala Leu Ile
            290                 295                 300

Asp Glu Ile Leu Ala Ala Leu Pro
305                 310

<210> SEQ ID NO 21
<211> LENGTH: 270
<212> TYPE: PRT
<213> ORGANISM: Artificial Sequence
<220> FEATURE:
<223> OTHER INFORMATION: Amino Acid Sequence of Second Polypeptide
      Chain of CD32B x CD79b (ABD) Diabody

<400> SEQUENCE: 21

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Asn Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Leu Thr Phe Gly Gly Gly Thr Lys Leu Glu Ile Lys
            100                 105                 110

Gly Gly Gly Ser Gly Gly Gly Gly Glu Val Gln Leu Val Glu Ser Gly
        115                 120                 125

Gly Gly Leu Val Gln Pro Gly Gly Ser Leu Arg Leu Ser Cys Ala Ala
    130                 135                 140

Ser Gly Phe Thr Phe Ser Asp Ala Trp Met Asp Trp Val Arg Gln Ala
145                 150                 155                 160

Pro Gly Lys Gly Leu Glu Trp Val Ala Glu Ile Arg Asn Lys Ala Lys
                165                 170                 175

Asn His Ala Thr Tyr Tyr Ala Glu Ser Val Ile Gly Arg Phe Thr Ile
            180                 185                 190

Ser Arg Asp Asp Ala Lys Asn Ser Leu Tyr Leu Gln Met Asn Ser Leu
        195                 200                 205

Arg Ala Glu Asp Thr Ala Val Tyr Tyr Cys Gly Ala Leu Gly Leu Asp
    210                 215                 220

Tyr Trp Gly Gln Gly Thr Leu Val Thr Val Ser Ser Gly Gly Cys Gly
225                 230                 235                 240

Gly Gly Lys Val Ala Ala Leu Lys Glu Lys Val Ala Ala Leu Lys Glu
                245                 250                 255

Lys Val Ala Ala Leu Lys Glu Lys Val Ala Ala Leu Lys Glu
            260                 265                 270

<210> SEQ ID NO 22
<211> LENGTH: 262
<212> TYPE: PRT
<213> ORGANISM: Artificial Sequence
<220> FEATURE:

<223> OTHER INFORMATION: Amino Acid Sequence of First Polypeptide Chain
of CD32B x CD79b Diabody

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Lys Ala Pro Arg Arg Leu Ile
        35                  40                  45

Tyr Ala Ala Ser Thr Leu Asp Ser Gly Val Pro Ser Arg Phe Ser Gly
    50                  55                  60

Ser Glu Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Phe Ser Tyr Pro Leu
                85                  90                  95

Thr Phe Gly Gly Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Met Asn Trp Val Arg Gln Ala Pro Gly Gln Gly Leu
145                 150                 155                 160

Glu Trp Ile Gly Met Ile Asp Pro Ser Asp Ser Glu Thr His Tyr Asn
                165                 170                 175

Gln Lys Phe Lys Asp Arg Val Thr Met Thr Thr Asp Thr Ser Thr Ser
            180                 185                 190

Thr Ala Tyr Met Glu Leu Arg Ser Leu Arg Ser Asp Asp Thr Ala Val
        195                 200                 205

Tyr Tyr Cys Ala Arg Ala Met Gly Tyr Trp Gly Gln Gly Thr Thr Val
    210                 215                 220

Thr Val Ser Ser Gly Gly Cys Gly Gly Gly Glu Val Ala Ala Leu Glu
225                 230                 235                 240

Lys Glu Val Ala Ala Leu Glu Lys Glu Val Ala Ala Leu Glu Lys Glu
                245                 250                 255

Val Ala Ala Leu Glu Lys
            260
```

<210> SEQ ID NO 23
<211> LENGTH: 1506
<212> TYPE: DNA
<213> ORGANISM: Artificial Sequence
<220> FEATURE:
<223> OTHER INFORMATION: Preferred Polynucleotide Encoding the
Polypeptide Chain of SEQ ID NO:15

<400> SEQUENCE: 23

```
gacaaaactc acacatgccc accgtgccca gcacctgaag ccgcgggggg accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
cgtgtggtca gcgtcctcac cgtcctgcac caggactggc tgaatggcaa ggagtacaag     300
tgcaaggtct ccaacaaagc cctcccagcc cccatcgaga aaaccatctc caaagccaaa     360
```

```
gggcagcccc gagaaccaca ggtgtacacc ctgcccccat cccgggagga gatgaccaag       420
aaccaggtca gcctgtggtg cctggtcaaa ggcttctatc ccagcgacat cgccgtggag       480
tgggagagca atgggcagcc ggagaacaac tacaagacca cgcctcccgt gctggactcc       540
gacggctcct tcttcctcta cagcaagctc accgtggaca agagcaggtg gcagcagggg       600
aacgtcttct catgctccgt gatgcatgag gctctgcaca accactacac gcagaagagc       660
ctctccctgt ctccgggtaa agccccttcc agctcccta tggaagacat ccagatgacc        720
cagtctccat cctccttatc tgcctctgtg ggagatagag tcaccatcac ttgtcgggca       780
agtcaggaaa ttagtggtta cttaagctgg ctgcagcaga aaccaggcaa ggcccctaga       840
cgcctgatct acgccgcatc cactttagat tctggtgtcc catccaggtt cagtggcagt       900
gagtctggga ccgagttcac cctcaccatc agcagcctc agcctgaaga ttttgcaacc        960
tattactgtc tacaatattt tagttatccg ctcacgttcg gaggggggac caaggtggaa      1020
ataaaaggag gcggatccgg cggcggaggc caggttcagc tggtgcagtc tggagctgag      1080
gtgaagaagc ctggcgcctc agtgaaggtc tcctgcaagg cttctggtta cacctttacc      1140
agctactgga tgaactgggt gcgacaggcc cctggacaag gcttgagtg gatcggaatg       1200 attgatcctt cagacagtga aactcactac aatcaaaagt tcaaggacag agtcaccatg      1260
accacagaca catccacgag cacagcctac atggagctga ggagcctgag atctgacgac      1320
acggccgtgt attactgtgc gagagctatg gctactgggg gcaagggac cacggtcacc       1380 gtctcctccg gaggatgtgg cggtggagaa gtggccgcac tggagaaaga ggttgctgct      1440
ttggagaagg aggtcgctgc acttgaaaag gaggtcgcag ccctggagaa aggcggcggg      1500
aactct                                                                 1506
```

<210> SEQ ID NO 24
<211> LENGTH: 810
<212> TYPE: DNA
<213> ORGANISM: Artificial Sequence
<220> FEATURE:
<223> OTHER INFORMATION: Preferred Polynucleotide Encoding the
      Polypeptide Chain of SEQ ID NO:16

<400> SEQUENCE: 24

```
gatgttgtga tgactcagtc tccactctcc ctgcccgtca cccttggaca gccggcctcc        60
atctcctgca gtcaagtca gagcctctta gatagtgatg gaaagacata tttgaattgg       120
tttcagcaga ggccaggcca atctccaaac cgcctaattt atctggtgtc taaactggac       180
tctggggtcc cagacagatt cagcggcagt gggtcaggca ctgatttcac actgaaaatc       240
agcagggtgg aggctgagga tgttggggtt tattactgct ggcaaggtac acattttccg       300
ctcacgttcg gcgagggac caagcttgag atcaaaggag gcggatccgg cggcggaggc       360
gaagtgcagc ttgtggagtc tggaggaggc ttggtgcaac tggaggatc cctgagactc       420 tcttgtgccg cctctggatt cacttttagt gacgcctgga tggactgggt ccgtcaggcc       480
ccaggcaagg gcttgagtg ggttgctgaa attagaaaca agctaaaaa tcatgcaaca       540 tactatgctg agtctgtgat agggaggttc accatctcaa gagatgacgc caaaacagt        600 ctgtacctgc aaatgaacag cttaagagct gaagacactg ccgtgtatta ctgtgggct       660 ctgggccttg actactgggg ccaaggcacc ctggtgaccg tctcctccgg aggatgtggc      720
ggtggaaaag tggccgcact gaaggagaaa gttgctgctt tgaaagagaa ggtcgccgca      780
cttaaggaaa aggtcgcagc cctgaaagag                                       810
```

-continued

```
<210> SEQ ID NO 25
<211> LENGTH: 681
<212> TYPE: DNA
<213> ORGANISM: Artificial Sequence
<220> FEATURE:
<223> OTHER INFORMATION: Preferred Polynucleotide Encoding the
      Polypeptide Chain of SEQ ID NO:17

<400> SEQUENCE: 25
gacaaaactc acacatgccc accgtgccca gcacctgaag ccgcgggggg accgtcagtc      60
ttcctcttcc ccccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggagga tgaccaag      420 aaccaggtca gcctgagttg cgcagtcaaa ggcttctatc ccagcgacat cgccgtggag    480
tgggagagca atgggcagcc ggagaacaac tacaagacca cgcctcccgt gctggactcc    540
gacggctcct tcttcctcgt cagcaagctc accgtggaca agagcaggtg gcagcagggg    600
aacgtcttct catgctccgt gatgcatgag gctctgcaca accgctacac gcagaagagc    660
ctctccctgt ctccgggtaa a                                              681
```

BI-SPECIFIC MONOVALENT FC DIABODIES THAT ARE CAPABLE OF BINDING CD32B AND CD79B AND USES THEREOF

CROSS-REFERENCE TO RELATED APPLICATIONS

This application is a § 371 National Stage Application of PCT/US2014/049848 (filed Aug. 6, 2014; pending) which application claims priority to U.S. Patent Applications No. 61/864,217 (filed on Aug. 9, 2013); 61/866,416 (filed on Aug. 15, 2013); 61/869,519 (filed on Aug. 23, 2013); and 61/907,525 (filed on Nov. 22, 2013), each of which applications is herein incorporated by reference in its entirety.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entirety.

BACKGROUND OF THE INVENTION

Field of the Invention

The present invention is directed to bi-specific monovalent diabodies that comprise an immunoglobulin Fc Domain ("bi-specific monovalent Fc diabodies") and are composed of three polypeptide chains and which possess at least one binding site specific for an epitope of CD32B and one binding site specific for an epitope of CD79b (i.e., a "CD32B×CD79b Fc diabody"). The bi-specific monovalent Fc diabodies of the present invention are capable of simultaneous binding to CD32B and CD79b. The invention is directed to such compositions, to pharmaceutical compositions that contain such bi-specific monovalent Fc diabodies and to methods for their use in the treatment of inflammatory diseases or conditions, and in particular, systemic lupus erythematosus (SLE) and graft vs. host disease.

Description of Related Art

I. The Fcγ Receptors and CD32B

The interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc Domain of antibodies or immune complexes to specialized cell-surface receptors on hematopoietic cells. The diversity of cellular responses triggered by antibodies and immune complexes results from the structural heterogeneity of Fc receptors. Fc receptors share structurally related ligand binding domains which presumably mediate intracellular signaling.

The Fc receptors are members of the immunoglobulin gene superfamily of proteins. They are surface glycoproteins that can bind the Fc portion of immunoglobulin molecules. Each member of the family recognizes immunoglobulins of one or more isotypes through a recognition domain on the a chain of the Fc receptor.

Fc receptors are defined by their specificity for immunoglobulin subtypes (see, Ravetch J. V. et al. (1991) "*Fc Receptors,*" Annu Rev. Immunol. 9:457-92; Gerber J. S. et al. (2001) "*Stimulatory And Inhibitory Signals Originating From The Macrophage Fcγ Receptors,*" Microbes and Infection, 3:131-139; Billadeau D. D. et al. (2002) "*ITAMs Versus ITIMs: Striking A Balance During Cell Regulation,*" J. Clin. Invest. 2(109):161-1681; Ravetch J. V. et al. (2000) "*Immune Inhibitory Receptors,*" Science 290:84-89; Ravetch J. V. et al. (2001) "*IgG Fc Receptors,*" Annu. Rev. Immunol. 19:275-90; Ravetch J. V. (1994) "*Fc Receptors: Rubor Redux,*" Cell, 78(4): 553-60).

Fc receptors that are capable of binding to IgG antibodies are termed "FcγRs." Each member of this family is an integral membrane glycoprotein, possessing extracellular domains related to a C2-set of immunoglobulin-related domains, a single membrane spanning domain and an intracytoplasmic domain of variable length. There are three known FcγRs, designated FcγRI(CD64), FcγRII(CD32), and FcγRIII(CD16). The three receptors are encoded by distinct genes; however, the extensive homologies between the three family members suggest they arose from a common progenitor perhaps by gene duplication.

FcγRII(CD32) proteins are 40 KDa integral membrane glycoproteins which bind only the complexed IgG due to a low affinity for monomeric Ig ($10^6$ $M^{-1}$). This receptor is the most widely expressed FcγR, present on all hematopoietic cells, including monocytes, macrophages, B cells, NK cells, neutrophils, mast cells, and platelets. FcγRII has only two immunoglobulin-like regions in its immunoglobulin binding chain and hence a much lower affinity for IgG than FcγRI. There are three human FcγRII genes (FcγRIIA(CD32A), FcγRIIB(CD32B), FcγRIIC(CD32C)), all of which bind IgG in aggregates or immune complexes.

Distinct differences within the cytoplasmic domains of the FcγRIIA and FcγRIIB create two functionally heterogenous responses to receptor ligation. The fundamental difference is that, upon binding to an IgG Fc region, the FcγRIIA isoform initiates intracellular signaling leading to immune system activation (e.g., phagocytosis, respiratory burst, etc.), whereas, upon binding to an IgG Fc region, the FcγRIIB isoform initiates signals that lead to the dampening or inhibition of the immune system (e.g., inhibiting B cell activation, etc.).

Such activating and inhibitory signals are both transduced through the FcγRs following ligation to an IgG Fc region. These diametrically opposing functions result from structural differences among the different receptor isoforms. Two distinct domains within the cytoplasmic signaling domains of the receptor called Immunoreceptor Tyrosine-based Activation Motifs (ITAMs) or Immunoreceptor Tyrosine-Based Inhibitory Motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB.

Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., $PI_3K$). Cellular activation leads to release of pro-inflammatory mediators.

The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. The molecular basis of this inhibition has been established. When FcγRIIB becomes co-ligated to an activating receptor by way of the Fc regions of the IgG immunoglobulins of an immune complex, the FcγRIIB ITIM becomes phosphorylated and attracts the SH2 domain of the inositol polyphosphate 5'-phosphatase (SHIP), which hydrolyzes phosphoinositol messengers released as a consequence of ITAM-containing, FcγR-mediated tyrosine kinase activation, consequently preventing the influx of intracellular $Ca^{++}$. Thus such cross-linking of FcγRIIB and an activating receptor dampens the activity of the activating receptor, and thus inhibits cellular responsiveness. Thus, on B-cells, B-cell activation, B-cell proliferation and antibody secretion is dampened or aborted. Thus, at the onset of antigen detection, monomeric IgG-antigen bonding occurs, and the Fc regions of bound antibodies bind to ITAMs of the activating FcγRs to mediate activation of the immune system. As the host's response progresses, multimeric IgG-antigen immune complexes form that are capable of binding to FcγRIIB (thus co-ligating such complexes with an activating receptor), leading to the dampening and ultimate cessation of the immune response (see, e.g., U.S. Pat. Nos. 8,445,645; 8,217,147; 8,216,579; 8,216,574; 8,193,318; 8,192,737; 8,187,593; 8,133,982; 8,044,180; 8,003,774; 7,960,512; 7,786,270; 7,632,497; 7,521,542; 7,425,619; 7,355,008 and United States Patent Publications No.: 2012/0276094; 2012/0269811; 2012/0263711; 2012/0219551; 2012/0213781; 2012/0141476; 2011/0305714; 2011/0243941; 2010/0322924; 2010/0254985; 2010/0196362; 2010/0174053; 2009/0202537; 2009/0191195; 2009/0092610; 2009/0076251; 2009/0074771; 2009/0060910; 2009/0053218; 2009/0017027; 2009/0017026; 2009/0017023; 2008/0138349; 2008/0138344; 2008/0131435; 2008/0112961; 2008/0044429; 2008/0044417; 2007/0077246; 2007/0036799; 2007/0014795; 2007/0004909; 2005/0260213; 2005/0215767; 2005/0064514; 2005/0037000; 2004/0185045).

II. The B-Cell Receptor and CD79b

B cells are immune system cells that are responsible for producing antibodies. The B-cell response to antigen is an essential component of the normal immune system. B-cells possess specialized cell-surface receptors (B-cell receptors; "BCR"). If a B-cell encounters an antigen capable of binding to that cell's BCR, the B-cell will be stimulated to proliferate and produce antibodies specific for the bound antigen. To generate an efficient response to antigens, BCR-associated proteins and T-cell assistance are also required. The antigen/BCR complex is internalized, and the antigen is proteolytically processed. A small part of the antigen remains complexed with major histocompatability complex-II ("MHC-II") molecules on the surface of the B cells where the complex can be recognized by T-cells. T-cells activated by such antigen presentation secrete a variety of lymphokines that induce B-cell maturation.

Signaling through the BCR plays an important role in the generation of antibodies, in autoimmunity, and in the establishment of immunological tolerance (Gauld, S. B. et al. (2002) *"B Cell Antigen Receptor Signaling: Roles In Cell Development And Disease,"* Science 296(5573):1641-1642). Immature B cells that bind self-antigens while still in the bone marrow are eliminated by apoptosis. In contrast, antigen binding on mature B cells results in activation, proliferation, anergy and apoptosis. The particular functional response observed depends upon whether the B-cell receives co-stimulatory signals through other surface receptors and the specific signal transduction pathways that are activated.

The BCR is composed of a membrane immunoglobulin which, together with non-covalently associated α and β subunits of CD79 ("CD79a" and "CD79b," respectively), forms the BCR complex. CD79a and CD79b are signal transducing subunits that contain a conserved immunoreceptor tyrosine-based activation motif ("ITAM") required for signal transduction (Dylke, J. et al. (2007) *"Role of the extracellular and transmembrane domain of Ig-alpha/beta in assembly of the B cell antigen receptor (BCR),"* Immunol. Lett. 112(1):47-57; Cambier, J. C. (1995) *"New Nomenclature For The Reth Motif (or ARH1/TAM/ARAM/YXXL),"* Immunol. Today 16:110). Aggregation of the BCR complex by multivalent antigen initiates transphosphorylation of the CD79a and CD79b ITAMs and activation of receptor-associated kinases (DeFranco, A. L. (1997) *"The Complexity Of Signaling Pathways Activated By The BCR,"* Curr. Opin. Immunol. 9:296-308; Kurosaki, T. (1997) *"Molecular Mechanisms In B-Cell Antigen Receptor Signaling,"* Curr. Opin. Immunol. 9:309-318; Kim, K. M. et al. (1993) *"Signalling Function Of The B-Cell Antigen Receptors,"* Immun. Rev. 132:125-146). Phosphorylated ITAMs recruit additional effectors such as $PI_3K$, PLC-γ and members of the Ras/MAPK pathway. These signaling events are responsible for both the B cell proliferation and increased expression of activation markers (such as MHC-II and CD86) that are required to prime B cells for their subsequent interactions with T-helper ("$T_h$") cells.

III. Inflammatory Diseases or Conditions

Inflammation is a process by which the body's white blood cells and chemicals protect our bodies from infection by foreign substances, such as bacteria and viruses. It is usually characterized by pain, swelling, warmth and redness of the affected area. Chemicals known as cytokines and prostaglandins control this process, and are released in an ordered and self-limiting cascade into the blood or affected tissues. This release of chemicals increases the blood flow to the area of injury or infection, and may result in the redness and warmth. Some of the chemicals cause a leak of fluid into the tissues, resulting in swelling. This protective process may stimulate nerves and cause pain. These changes, when occurring for a limited period in the relevant area, work to the benefit of the body.

Inflammatory diseases or conditions reflect an immune system attack on a body's own cells and tissue (i.e., an "autoimmune" response). There are many different autoimmune disorders which affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin. Examples of autoimmune disorders include, but are not limited to, Hashimoto's thyroiditis, pernicious anemia, Addison's disease, type 1 diabetes, rheumatoid arthritis, systemic lupus erythematosus (SLE), dermatomyositis, Sjogren's syndrome, dermatomyositis, lupus erythematosus, multiple sclerosis, autoimmune inner ear disease myasthenia gravis, Reiter's syndrome, Graves' disease, autoimmune hepatitis, familial adenomatous polyposis and ulcerative colitis.

Inflammatory diseases or conditions can also arise when the body's normally protective immune system causes damage by attacking foreign cells or tissues whose presence is beneficial to the body (e.g., the rejection of transplants (host vs. host disease)) or from the rejection of the cells of an immunosuppressed host by immunocompetent cells of an introduced transplant graft (graft vs. host disease) (DePaoli, A. M. et al. (1992) "Graft-Versus-Host Disease And Liver Transplantation," Ann. Intern. Med. 117:170-171; Sudhindran, S. et al. (2003) "Treatment Of Graft-Versus-Host Disease After Liver Transplantation With Basiliximab Followed By Bowel Resection," Am J Transplant. 3:1024-1029; Pollack, M. S. et al. (2005) "Severe, Late-Onset Graft-Versus-Host Disease In A Liver Transplant Recipient Documented By Chimerism Analysis," Hum. Immunol. 66:28-31; Perri, R. et al. (2007) "Graft Vs. Host Disease After Liver Transplantation: A New Approach Is Needed," Liver Transpl. 13:1092-1099; Mawad, R. et al. (2009) "Graft-Versus-Host Disease Presenting With Pancytopenia After En Bloc Multiorgan Transplantation: Case Report And Literature Review," Transplant Proc. 41:4431-4433; Akbulut, S. et al. (2012) "Graft-Versus-Host Disease After Liver Transplantation: A Comprehensive Literature Review," World J. Gastroenterol. 18(37): 5240-5248).

Despite recent advances in the treatment of such diseases or conditions, a need continues to exist for compositions capable of treating or preventing inflammatory diseases or conditions.

IV. Bi-Specific Diabodies

The ability of an intact, unmodified antibody (e.g., an IgG) to bind an epitope of an antigen depends upon the presence of variable domains on the immunoglobulin light and heavy chains (i.e., the VL and VH Domains, respectively). The design of a diabody is based on the single chain Fv construct (scFv) (see, e.g., Holliger et al. (1993) "'Diabodies': Small Bivalent And Bispecific Antibody Fragments," Proc. Natl. Acad. Sci. (U.S.A.) 90:6444-6448; US 2004/0058400 (Hollinger et al.); US 2004/0220388 (Mertens et al.); Alt et al. (1999) FEBS Lett. 454(1-2):90-94; Lu, D. et al. (2005) "A Fully Human Recombinant IgG-Like Bispecific Antibody To Both The Epidermal Growth Factor Receptor And The Insulin-Like Growth Factor Receptor For Enhanced Antitumor Activity," J. Biol. Chem. 280(20):19665-19672; WO 02/02781 (Mertens et al.); Olafsen, T. et al. (2004) "Covalent Disulfide-Linked Anti-CEA Diabody Allows Site-Specific Conjugation And Radiolabeling For Tumor Targeting Applications," Protein Eng Des Sel. 17(1): 21-27; Wu, A. et al. (2001) "Multimerization Of A Chimeric Anti-CD20 Single Chain Fv-Fv Fusion Protein Is Mediated Through Variable Domain Exchange," Protein Engineering 14(2):1025-1033; Asano et al. (2004) "A Diabody For Cancer Immunotherapy And Its Functional Enhancement By Fusion Of Human Fc Region," Abstract 3P-683, J. Biochem. 76(8):992; Takemura, S. et al. (2000) "Construction Of A Diabody (Small Recombinant Bispecific Antibody) Using A Refolding System," Protein Eng. 13(8):583-588; Baeuerle, P. A. et al. (2009) "Bispecific T-Cell Engaging Antibodies For Cancer Therapy," Cancer Res. 69(12):4941-4944).

Interaction of an antibody light chain and an antibody heavy chain and, in particular, interaction of its VL and VH Domains forms one of the epitope binding sites of the antibody. In contrast, the scFv construct comprises VL and VH Domains of an antibody contained in a single polypeptide chain wherein the domains are separated by a flexible linker of sufficient length to allow self-assembly of the two domains into a functional epitope binding site. Where self-assembly of the VL and VH Domains is rendered impossible due to a linker of insufficient length (less than about 12 amino acid residues), two of the scFv constructs interact with one another other to form a bivalent molecule in which the VL Domain of one chain associates with the VH Domain of the other (reviewed in Marvin et al. (2005) "Recombinant Approaches To IgG-Like Bispecific Antibodies," Acta Pharmacol. Sin. 26:649-658).

Natural antibodies are capable of binding to only one epitope species (i.e., mono-specific), although they can bind multiple copies of that species (i.e., exhibiting bi-valency or multi-valency). The art has noted the capability to produce diabodies that differ from such natural antibodies in being capable of binding two or more different epitope species (i.e., exhibiting bi-specificity or multispecificity in addition to bi-valency or multi-valency) (see, e.g., Holliger et al. (1993) "'Diabodies': Small Bivalent And Bispecific Antibody Fragments," Proc. Natl. Acad. Sci. (U.S.A.) 90:6444-6448; US 2004/0058400 (Hollinger et al.); US 2004/0220388 (Mertens et al.); Alt et al. (1999) FEBS Lett. 454(1-2):90-94; Lu, D. et al. (2005) "A Fully Human Recombinant IgG-Like Bispecific Antibody To Both The Epidermal Growth Factor Receptor And The Insulin-Like Growth Factor Receptor For Enhanced Antitumor Activity," J. Biol. Chem. 280(20):19665-19672; WO 02/02781 (Mertens et al.); Mertens, N. et al., "New Recombinant Bi-and Trispecific Antibody Derivatives," In: NOVEL FRONTIERS IN THE PRODUCTION OF COMPOUNDS FOR BIOMEDICAL USE, A. VanBroekhoven et al. (Eds.), Kluwer Academic Publishers, Dordrecht, The Netherlands (2001), pages 195-208; Wu, A. et al. (2001) "Multimerization Of A Chimeric Anti-CD20 Single Chain Fv-Fv Fusion Protein Is Mediated Through Variable Domain Exchange," Protein Engineering 14(2): 1025-1033; Asano et al. (2004) "A Diabody For Cancer Immunotherapy And Its Functional Enhancement By Fusion Of Human Fc Region," Abstract 3P-683, J. Biochem. 76(8): 992; Takemura, S. et al. (2000) "Construction Of A Diabody (Small Recombinant Bispecific Antibody) Using A Refolding System," Protein Eng. 13(8):583-588; Baeuerle, P. A. et al. (2009) "Bispecific T-Cell Engaging Antibodies For Cancer Therapy," Cancer Res. 69(12):4941-4944).

The provision of non-monospecific diabodies provides a significant advantage: the capacity to co-ligate and co-localize cells that express different epitopes. Bivalent diabodies thus have wide-ranging applications including therapy and immunodiagnosis. Bi-valency allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "Improved Tumour Targeting By Disulphide Stabilized Diabodies Expressed In Pichia pastoris," Protein Eng. 10:1221). Of particular importance is the co-ligating of differing cells, for example, the cross-linking of cytotoxic T-cells to tumor cells (Staerz et al. (1985) "Hybrid Antibodies Can Target Sites For Attack By T Cells," Nature 314: 628-631, and Holliger et al. (1996) "Specific Killing Of Lymphoma Cells By Cytotoxic T-Cells Mediated By A Bispecific Diabody," Protein Eng. 9:299-305).

Diabody epitope binding domains may also be directed to a surface determinant of any immune effector cell such as CD3, CD16, CD32, or CD64, which are expressed on T lymphocytes, natural killer (NK) cells or other mononuclear cells. In many studies, diabody binding to effector cell determinants, e.g., Fcγ receptors (FcγR), was also found to activate the effector cell (Holliger et al. (1996) "Specific Killing Of Lymphoma Cells By Cytotoxic T-Cells Mediated By A Bispecific Diabody," Protein Eng. 9:299-305; Holliger et al. (1999) "Carcinoembryonic Antigen (CEA)-Specific T-cell Activation In Colon Carcinoma Induced By Anti-CD3×Anti-CEA Bispecific Diabodies And B7×Anti-CEA Bispecific Fusion Proteins," Cancer Res. 59:2909-2916; WO 2006/113665; WO 2008/157379; WO 2010/080538; WO 2012/018687; WO 2012/162068). Normally, effector cell activation is triggered by the binding of an antigen bound antibody to an effector cell via Fc-FcγR interaction; thus, in this regard, diabody molecules of the invention may exhibit Ig-like functionality independent of whether they comprise an Fc Domain (e.g., as assayed in any effector function assay known in the art or exemplified herein (e.g., ADCC assay)). By cross-linking tumor and effector cells, the diabody not only brings the effector cell within the proximity of the tumor cells but leads to effective tumor killing (see e.g., Cao et al. (2003) "Bispecific Antibody Conjugates In Therapeutics," Adv. Drug. Deliv. Rev. 55:171-197).

However, the above advantages come at salient cost. The formation of such non-monospecific diabodies requires the successful assembly of two or more distinct and different polypeptides (i.e., such formation requires that the diabodies be formed through the heterodimerization of different polypeptide chain species). This fact is in contrast to mono-specific diabodies, which are formed through the homodimerization of identical polypeptide chains. Because at least two dissimilar polypeptides (i.e., two polypeptide species) must be provided in order to form a non-monospecific diabody, and because homodimerization of such polypeptides leads to inactive molecules (Takemura, S. et al. (2000) "Construction Of A Diabody (Small Recombinant Bispecific Antibody) Using A Refolding System," Protein Eng. 13(8): 583-588), the production of such polypeptides must be accomplished in such a way as to prevent covalent bonding between polypeptides of the same species (Takemura, S. et al. (2000) "Construction Of A Diabody (Small Recombinant Bispecific Antibody) Using A Refolding System," Protein Eng. 13(8):583-588). The art has therefore taught the non-covalent association of such polypeptides (see, e.g., Olafsen et al. (2004) "Covalent Disulfide-Linked Anti-CEA Diabody Allows Site-Specific Conjugation And Radiolabeling For Tumor Targeting Applications," Prot. Engr. Des. Sel. 17:21-27; Asano et al. (2004) "A Diabody For Cancer Immunotherapy And Its Functional Enhancement By Fusion Of Human Fc Region," Abstract 3P-683, J. Biochem. 76(8): 992; Takemura, S. et al. (2000) "Construction Of A Diabody (Small Recombinant Bispecific Antibody) Using A Refolding System," Protein Eng. 13(8):583-588; Lu, D. et al. (2005) "A Fully Human Recombinant IgG-Like Bispecific Antibody To Both The Epidermal Growth Factor Receptor And The Insulin-Like Growth Factor Receptor For Enhanced Antitumor Activity," J. Biol. Chem. 280(20): 19665-19672).

However, the art has recognized that bi-specific diabodies composed of non-covalently associated polypeptides are unstable and readily dissociate into non-functional monomers (see, e.g., Lu, D. et al. (2005) "A Fully Human Recombinant IgG-Like Bispecific Antibody To Both The Epidermal Growth Factor Receptor And The Insulin-Like Growth Factor Receptor For Enhanced Antitumor Activity," J. Biol. Chem. 280(20):19665-19672).

In the face of this challenge, the art has succeeded in developing stable, covalently bonded heterodimeric non-monospecific diabodies (see, e.g., WO 2006/113665; WO/2008/157379; WO 2010/080538; WO 2012/018687; WO/2012/162068; Johnson, S. et al. (2010) "Effector Cell Recruitment With Novel Fv-Based Dual-Affinity Re-Targeting Protein Leads To Potent Tumor Cytolysis And In Vivo B-Cell Depletion," J. Molec. Biol. 399(3):436-449; Veri, M. C. et al. (2010) "Therapeutic Control Of B Cell Activation Via Recruitment Of Fcgamma Receptor IIb (CD32B) Inhibitory Function With A Novel Bispecific Antibody Scaffold," Arthritis Rheum. 62(7):1933-1943; Moore, P. A. et al. (2011) "Application Of Dual Affinity Retargeting Molecules To Achieve Optimal Redirected T-Cell Killing Of B-Cell Lymphoma," Blood 117(17):4542-4551). Such approaches involve engineering one or more cysteine residues into each of the employed polypeptide species. For example, the addition of a cysteine residue to the C-terminus of such constructs has been shown to allow disulfide bonding between the polypeptide chains, stabilizing the resulting heterodimer without interfering with the binding characteristics of the bivalent molecule.

Notwithstanding such success, the production of stable, functional heterodimeric, non-monospecific can be further improved by the careful consideration and placement of the domains employed in the polypeptide chains. The present invention is thus directed to the provision of specific polypeptides that are particularly designed to form, via covalent bonding, heterodimeric Fc diabodies that are capable of simultaneously binding CD32B and CD79b.

SUMMARY OF THE INVENTION

The invention is directed to CD32B×CD79b bi-specific monovalent diabodies that comprise an immunoglobulin Fc region ("CD32B×CD79b bi-specific monovalent Fc diabodies"). The CD32B×CD79b bi-specific monovalent Fc diabodies of the invention are composed of three polypeptide chains (a "first," "second" and "third" polypeptide chain), wherein the first and second polypeptide chains are covalently bonded to one another and the first and third polypeptide chains are covalently bonded to one another. Such covalent bondings are, for example, by disulfide bonding of cysteine residues located within each polypeptide chain. The first and second polypeptide chains of the CD32B×CD79b bi-specific monovalent Fc diabodies of the invention associate with one another in a heterodimeric manner to form one binding site specific for an epitope of CD32B and one binding site specific for an epitope of CD79b. The CD32B×CD79b bi-specific monovalent Fc diabodies of the invention are thus monovalent in that they are capable of binding to only one copy of an epitope of CD32B and to only one copy of an epitope of CD79b, but bi-specific in that a single diabody is able to bind simultaneously to the epitope of CD32B and to the epitope of CD79b. The bi-specific monovalent Fc diabodies of the present invention are capable of simultaneous binding to CD32B and CD79b. The invention is directed to such CD32B×CD79b bi-specific monovalent Fc diabodies, and to pharmaceutical compositions that contain such bi-specific monovalent Fc diabodies The invention is additionally directed to methods for the use of such diabodies in the treatment of inflammatory diseases or conditions, and in particular, systemic lupus erythematosus (SLE) and graft vs. host disease.

In detail, the invention provides a bi-specific monovalent Fc diabody, wherein the bi-specific monovalent Fc diabody is capable of specific binding to an epitope of CD32B and to an epitope of CD79b, and possesses an IgG Fc Domain, wherein the bi-specific monovalent Fc diabody comprises a first polypeptide chain, a second polypeptide chain and a third polypeptide chain, wherein the first and second polypeptide chains are covalently bonded to one another and the first and third polypeptide chains are covalently bonded to one another, and wherein:

A. the first polypeptide chain comprises, in the N-terminal to C-terminal direction:
  i. a Domain 1, comprising:
    (1) a sub-Domain (1A), which comprises a cysteine-containing peptide (especially, a peptide having the sequence of (Peptide 1) SEQ ID NO:1); and
    (2) a sub-Domain (1B), which comprises a polypeptide portion of an IgG Fc Domain (most preferably, having CH2 and CH3 domains of an IgG immunoglobulin Fc region);
  ii. a Domain 2, comprising:
    (1) a sub-Domain (2A), which comprises a VL Domain of a monoclonal antibody capable of binding to CD32B (VL$_{CD32B}$) (SEQ ID NO:11); and
    (2) a sub-Domain (2B), which comprises a VH Domain of a monoclonal antibody capable of binding to CD79b (VH$_{CD79b}$) (SEQ ID NO:14),
    wherein the sub-Domains (2A) and (2B) are separated from one another by a peptide linker (especially, a peptide linker (Linker 2) having the sequence of SEQ ID NO:4);
  iii. a Domain 3, wherein the Domain 3 is an E-coil Domain (SEQ ID NO:7) or a K-coil Domain (SEQ ID NO:8), wherein the Domain 3 is separated from the Domain 2 by a peptide linker (especially, a peptide linker having the sequence of SEQ ID NO:5); and
  iv. a C-terminal spacer peptide (especially, a spacer peptide having the sequence of SEQ ID NO:6);
B. the second polypeptide chain comprises, in the N-terminal to C-terminal direction:
  i. a Domain 1, comprising:
    (1) a sub-Domain (1A), which comprises a VL Domain of a monoclonal antibody capable of binding to CD79b (VL$_{CD79b}$) (SEQ ID NO:13); and
    (2) a sub-Domain (1B), which comprises a VH Domain of a monoclonal antibody capable of binding to CD32B (VH$_{CD32B}$) (SEQ ID NO:12);
    wherein the sub-Domains (1A) and (1B) are separated from one another by a peptide linker (especially, a peptide linker (Linker 2) having the sequence of SEQ ID NO:4);
  ii. a Domain 2, wherein the Domain 2 is a K-coil Domain (SEQ ID NO:8) or an E-coil Domain (SEQ ID NO:7), wherein the Domain 2 is separated from the Domain 1 by a peptide linker (especially, a peptide linker having the sequence of SEQ ID NO:5); and wherein the Domain 3 of the first polypeptide chain and the Domain 2 of the second polypeptide chain are not both E-coil Domains or both K-coil Domains; and
C. the third polypeptide chain comprises, in the N-terminal to C-terminal direction, a Domain 1 comprising:
  (1) a sub-Domain (1A), which comprises a cysteine-containing peptide (especially, a peptide linker having the sequence of (Peptide 1) SEQ ID NO:1); and
  (2) a sub-Domain (1B), which comprises a polypeptide portion of an IgG Fc Domain (most preferably, having CH2 and CH3 domains of an IgG immunoglobulin Fc region);
and wherein:
(a) the polypeptide portions of the IgG Fc Domains of the first and third polypeptide chain form the IgG Fc Domain;
(b) the VL Domain of the first polypeptide chain and the VH Domain of the second polypeptide chain form an Antigen-Binding Domain capable of specific binding to an epitope of CD32B; and
(c) the VH Domain of the first polypeptide chain and the VL Domain of the second polypeptide chain form an Antigen-Binding Domain capable of specific binding to an epitope of CD79b.

The invention additionally provides a bi-specific monovalent Fc diabody, wherein the bi-specific monovalent Fc diabody is capable of specific binding to an epitope of CD32B and to an epitope of CD79b, and possesses an IgG Fc Domain, wherein the bi-specific monovalent Fc diabody comprises a first polypeptide chain, a second polypeptide chain and a third polypeptide chain, wherein the first and second polypeptide chains are covalently bonded to one another and the first and third polypeptide chains are covalently bonded to one another, and wherein:

A. the first polypeptide chain comprises, in the N-terminal to C-terminal direction:
  i. a Domain 1, comprising:
    (1) a sub-Domain (1A), which comprises a cysteine-containing peptide (especially, a peptide linker having the sequence of (Peptide 1) SEQ ID NO:1); and
    (2) a sub-Domain (1B), which comprises a polypeptide portion of an IgG Fc Domain (most preferably, having CH2 and CH3 domains of an IgG immunoglobulin Fc region);
  ii. a Domain 2, comprising:
    (1) a sub-Domain (2A), which comprises a VL Domain of a monoclonal antibody capable of binding to CD79b (VL$_{CD79b}$) (SEQ ID NO:13); and
    (2) a sub-Domain (2B), which comprises a VH Domain of a monoclonal antibody capable of binding to CD32B (VH$_{CD32B}$) (SEQ ID NO:12);
    wherein the sub-Domains (2A) and (2B) are separated from one another by a peptide linker (especially, a peptide linker having the sequence of SEQ ID NO:4);
  iii. a Domain 3, wherein the Domain 3 is an E-coil Domain (SEQ ID NO:7) or a K-coil Domain (SEQ ID NO:8), wherein the Domain 3 is separated from the Domain 2 by a peptide (especially, a peptide linker having the sequence of SEQ ID NO:5); and
  iv. a C-terminal spacer peptide (especially, a spacer peptide having the sequence of SEQ ID NO:6);
B. the second polypeptide chain comprises, in the N-terminal to C-terminal direction:
  i. a Domain 1, comprising:
    (1) a sub-Domain (1A), which comprises a VL Domain of a monoclonal antibody capable of binding to CD32B (VL$_{CD32B}$) (SEQ ID NO:11); and
    (2) a sub-Domain (1B), which comprises a VH Domain of a monoclonal antibody capable of binding to CD79b (VH$_{CD79b}$) (SEQ ID NO:14);
    wherein the sub-Domains (1A) and (1B) are separated from one another by a peptide linker (especially, a peptide linker having the sequence of SEQ ID NO:4);
  ii. a Domain 2, wherein the Domain 2 is a K-coil Domain (SEQ ID NO:8) or an E-coil Domain (SEQ ID NO:7), wherein the Domain 2 is separated from the Domain 1 by a peptide linker (especially, a peptide linker having the sequence of SEQ ID NO:5); and wherein the Domain 3 of the first polypeptide chain and the Domain 2 of the second polypeptide chain are not both E-coil Domains or both K-coil Domains; and C. the third polypeptide chain comprises, in the N-terminal to C-terminal direction, a Domain 1 comprising:
  (1) a sub-Domain (1A), which comprises a cysteine-containing peptide (especially, a peptide linker having the sequence of (Peptide 1) SEQ ID NO:1); and
  (2) a sub-Domain (1B), which comprises a polypeptide portion of an IgG Fc Domain (most preferably, having CH2 and CH3 domains of an IgG immunoglobulin Fc region);
and wherein:
(a) the polypeptide portions of the Fc Domains of the first and third polypeptide chain form the IgG Fc region;
(b) the VL Domain of the first polypeptide chain and the VH Domain of the second polypeptide chain form an Antigen-Binding Domain capable of specific binding to an epitope of CD79b; and
(c) the VH Domain of the first polypeptide chain and the VL Domain of the second polypeptide chain form an Antigen-Binding Domain capable of specific binding to an epitope of CD32B.

The invention further concerns the embodiments of all such bi-specific monovalent Fc diabodies, wherein the Domain 1 of the first polypeptide chain comprises a sequence different from that of the Domain 1 of the third polypeptide chain.

The invention further concerns the embodiments of all such bi-specific monovalent Fc diabodies wherein said sub-Domain (1B) of said first polypeptide chain has the amino acid sequence of SEQ ID NO:9, and said sub-Domain (1B) of said third polypeptide chain has the amino acid sequence of SEQ ID NO:10.

The invention further concerns the embodiments of all such bi-specific monovalent Fc diabodies wherein said sub-Domain (1B) of said first polypeptide chain has the amino acid sequence of SEQ ID NO:10, and said sub-Domain (1B) of said third polypeptide chain has the amino acid sequence of SEQ ID NO:9.

The invention further concerns the embodiments of all such bi-specific monovalent Fc diabodies, wherein the Domain 1 of the first polypeptide chain and/or the Domain 1 of the third polypeptide chain comprises a variant CH2-CH3 sequence that exhibits altered binding to an Fcγ receptor.

The invention further concerns the embodiments of all such bi-specific monovalent Fc diabodies wherein the Domain 3 of the first polypeptide chain comprises an E-coil (SEQ ID NO:7), and the Domain 2 of the second polypeptide chain comprises a K-coil (SEQ ID NO:8).

The invention further concerns the embodiments of all such bi-specific monovalent Fc diabodies wherein the Domain 3 of the first polypeptide chain comprises a K-coil (SEQ ID NO:8), and the Domain 2 of the second polypeptide chain comprises an E-coil (SEQ ID NO:7).

The invention further provides a bi-specific monovalent diabody comprising an IgG immunoglobulin Fc (bi-specific monovalent Fc diabody), wherein the bi-specific monovalent Fc diabody comprises:
(1) a first polypeptide chain having the amino acid sequence of SEQ ID NO:15;
(2) a second polypeptide chain having the amino acid sequence of SEQ ID NO:16; and
(3) a third polypeptide chain having the amino acid sequence of SEQ ID NO:17, wherein amino acid residues 1-10 of said third polypeptide chain are Peptide 1 (SEQ ID NO:1), and amino acid residues 11-227 of said third polypeptide chain are the CH2 and CH3 domains of an IgG antibody Fc region (SEQ ID NO:10);

wherein the first and the second polypeptide chains are covalently bonded to one another by a first disulfide bond and the first and third polypeptide chains are covalently bonded to one another by a second disulfide bond.

The invention further provides a pharmaceutical composition comprising any of the above-described bi-specific monovalent Fc diabodies and a physiologically acceptable carrier.

The invention further provides for the use of such pharmaceutical composition in the treatment of an inflammatory disease or condition, especially wherein the inflammatory disease or condition is an autoimmune disease, and in particular, wherein the autoimmune disease is systemic lupus erythematosus (SLE).

The invention further provides for the use of such pharmaceutical composition in the treatment of an inflammatory disease or condition, especially wherein the inflammatory disease or condition is graft vs. host disease (GvHD).

DETAILED DESCRIPTION OF THE INVENTION

The present invention is directed to bi-specific monovalent diabodies that comprise an immunoglobulin Fc Domain ("bi-specific monovalent Fc diabodies") and are composed of three polypeptide chains and which possess at least one binding site specific for an epitope of CD32B and one binding site specific for an epitope of CD79b (i.e., a "CD32B×CD79b Fc diabody"). The bi-specific monovalent Fc diabodies of the present invention are capable of simultaneous binding to CD32B and CD79b. The invention is directed to such compositions, to pharmaceutical compositions that contain such bi-specific monovalent Fc diabodies and to methods for their use in the treatment of inflammatory diseases or conditions, and in particular, systemic lupus erythematosus (SLE) and graft vs. host disease.

As indicated above, CD79b is expressed by B cells, and is thus expressed on cells that are proliferating in response to antigen recognition. Antibodies capable of immunospecifically binding to CD79b are capable of binding to such B cells. CD32B is an FcγR and is expressed on B cells. Antibodies capable of immunospecifically binding to FcγRIIB(CD32B) and particularly such antibodies that bind to FcγRIIB without substantially interfering or impeding Fc binding are capable of increasing the ability of FcγRIIB to co-ligate with activating receptors of immune complexes. A bi-specific monovalent Fc diabody that is capable of binding to both CD32B and CD79b, has the ability to inhibit or dampen a host's immune system in response to an unwanted B cell activation, B cell proliferation and antibody secretion. Such bi-specific monovalent Fc diabodies thus have utility in the treatment of inflammatory diseases and disorders.

I. Preferred CD32B×CD79b Fc Diabodies of the Present Invention

Figure 1:
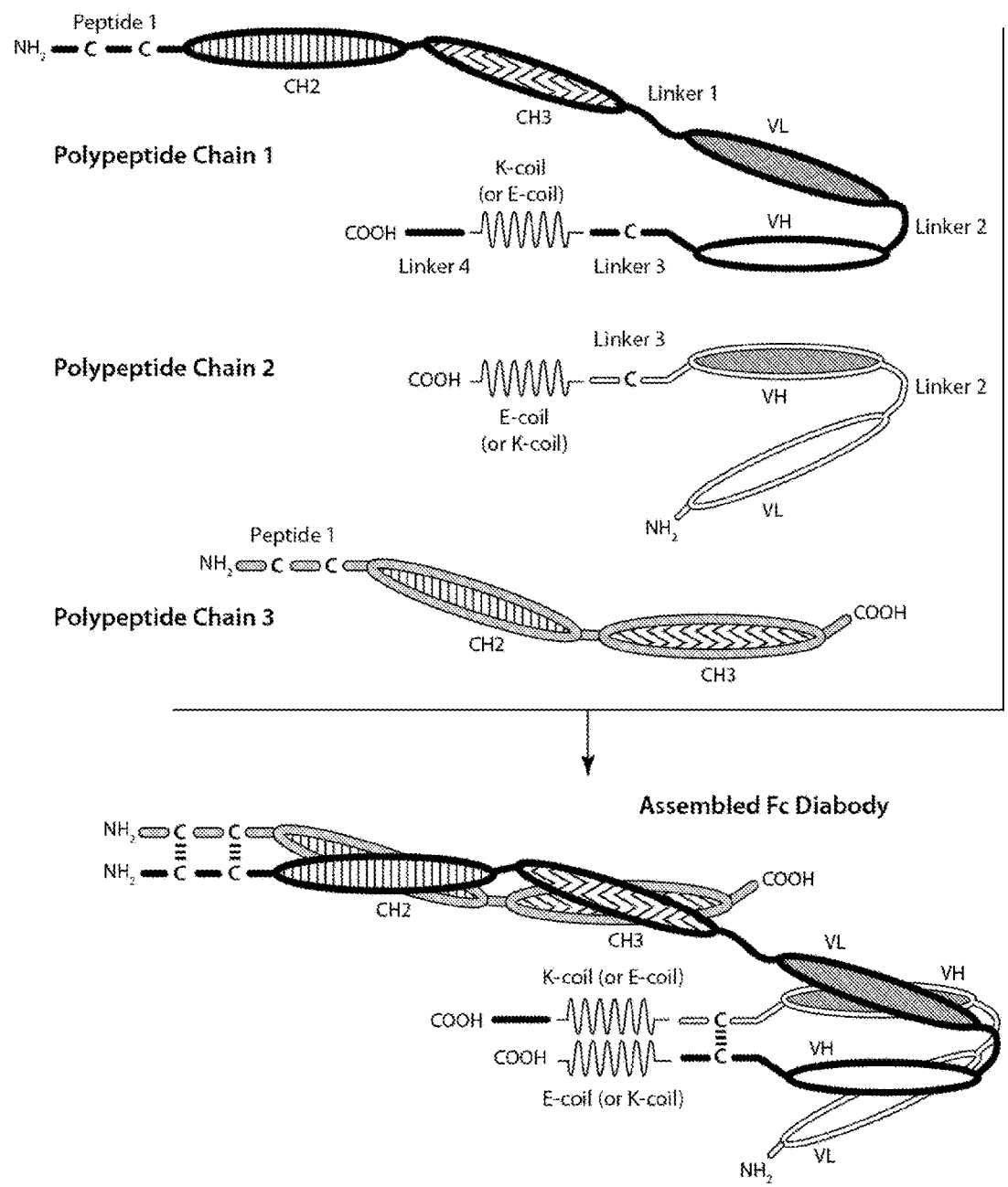
FIG. 1 illustrates the three polypeptide chains of a preferred bi-specific monovalent Fc diabody and the structure of the covalently associated chains.

The preferred CD32B×CD79b Fc diabodies of the present invention are termed "Fc" diabodies, because they comprise an Fc Domain. As shown schematically in FIG. 1, such Fc diabodies are composed of three polypeptide chains, of which the first and second polypeptide chains are covalently bonded to one another and the first and third polypeptide chains are bonded to one another. The VL Domain of the first polypeptide chain interacts with the VH Domain of the second polypeptide chain in order to form a first functional antigen binding site that is specific for the first antigen (i.e., either CD32B or CD79b). Likewise, the VL Domain of the second polypeptide chain interacts with the VH Domain of the first polypeptide chain in order to form a second functional antigen binding site that is specific for the second antigen (i.e., either CD79b or CD32B, depending upon the identity of the first antigen). Thus, the selection of the VL and VH Domains of the first and second polypeptide chains are coordinated, such that the two polypeptide chains collectively comprise VL and VH Domains capable of binding to CD32B and CD79b (i.e., they comprise $VL_{CD32B}/VH_{CD32B}$ and $VL_{CD79b}/VH_{CD79b}$) (FIG. 1). Collectively, each such VL and VH Domain, and the intervening Linker that separates them, are referred to as an Antigen-Binding Domain of the molecule.

The Fc Domain of the Fc diabodies of the present invention may be either a complete Fc region (e.g., a complete IgG Fc region) or only a fragment of a complete Fc region. Although the Fc Domain of the bi-specific monovalent Fc diabodies of the present invention may possess the ability to bind to one or more Fc receptors (e.g., FcγR(s)), more preferably such Fc Domain will cause reduced binding to FcγRIA (CD64), FcγRIIA (CD32A), FcγRIIB (CD32B), FcγRIIIA (CD16a) or FcγRIIIB (CD16b) (relative to the binding exhibited by a wild-type Fc region) or will substantially eliminate the ability of such Fc Domain to bind to such receptor(s). The Fc Domain of the bi-specific monovalent Fc diabodies of the present invention may include some or all of the CH2 domain and/or some or all of the CH3 domain of a complete Fc region, or may comprise a variant CH2 and/or a variant CH3 sequence (that may include, for example, one or more insertions and/or one or more deletions with respect to the CH2 or CH3 domains of a complete Fc region). The Fc Domain of the bi-specific monovalent Fc diabodies of the present invention may comprise non-Fc polypeptide portions, or may comprise portions of non-naturally complete Fc regions, or may comprise non-naturally occurring orientations of CH2 and/or CH3 domains (such as, for example, two CH2 domains or two CH3 domains, or in the N-terminal to C-terminal direction, a CH3 domain linked to a CH2 domain, etc.).

The first polypeptide chain of the preferred CD32B× CD79b bi-specific monovalent Fc diabody comprises (in the N-terminal to C-terminal direction): an amino terminus, a cysteine-containing peptide (Peptide 1), an IgG Fc Domain (preferably, the CH2 and CH3 domains of an antibody Fc region, and most preferably the CH2 and CH3 domains of an antibody Fc region that will cause reduced binding to FcγRIA (CD64), FcγRIIA (CD32A), FcγRIIB (CD32B), FcγRIIIA (CD16a) or FcγRIIIB (CD16b) (relative to the binding exhibited by a wild-type Fc region) or will substantially eliminate the ability of such Fc Domain to bind to such receptor(s), a first intervening spacer peptide (Linker 1), the VL Domain of a monoclonal antibody capable of binding to either CD32B or CD79b (i.e., either $VL_{CD32B}$ or $VL_{CD79b}$), a second intervening spacer peptide (Linker 2), a VH Domain of a monoclonal antibody capable of binding to either CD79b (if such first polypeptide chain contains $VL_{CD32B}$) or CD32B (if such first polypeptide chain contains $VL_{CD79b}$), a cysteine-containing third intervening spacer peptide (Linker 3), a heterodimer-promoting domain, an optional fourth spacer peptide (Linker 4) to provide improved stabilization to the heterodimer-promoting domain and a C-terminus (FIG. 1).

The second polypeptide chain of the preferred CD32B× CD79b bi-specific monovalent Fc diabody comprises (in the N-terminal to C-terminal direction): an amino terminus, a VL Domain of a monoclonal antibody capable of binding to either CD79b or CD32B (i.e., either $VL_{CD79b}$ or $VL_{CD32B}$, depending upon the VL Domain selected for the first polypeptide chain of the diabody), an intervening linker peptide (Linker 2), a VH Domain of a monoclonal antibody capable of binding to either CD32B (if such second polypeptide chain contains $VL_{CD79b}$) or CD32B (if such second polypeptide chain contains $VL_{CD32B}$), a cysteine-containing spacer peptide (Linker 3), a heterodimer-promoting domain, and a C-terminus (FIG. 1).

The third polypeptide chain of the preferred CD32B× CD79b bi-specific monovalent Fc diabody comprises (in the N-terminal to C-terminal direction): an amino terminus, a cysteine-containing peptide (Peptide 1), an IgG Fc Domain (preferably, the CH2 and CH3 domains of an antibody Fc region) having the same isotype as that of the Fc Domain of the first polypeptide chain and a C-terminus. Preferably, the Fc Domain of the third polypeptide chain will cause reduced binding to FcγRIA (CD64), FcγRIIA (CD32A), FcγRIIB (CD32B), FcγRIIIA (CD16a) or FcγRIIIB (CD16b) (relative to the binding exhibited by a wild-type Fc region) or will substantially eliminate the ability of such Fc Domain to bind to such receptor(s) (FIG. 1).

The cysteine-containing peptide (Peptide 1) of the first and third stands may be comprised of the same amino acid sequence or of different amino acid sequences, and will contain 1, 2, 3 or more cysteine residues. A particularly preferred Peptide 1 has the amino acid sequence (SEQ ID NO:1): DKTHTCPPCP. The first intervening spacer peptide (Linker 1) comprises the amino acid sequence (SEQ ID NO:2): APSSS, and more preferably has the amino acid sequence (SEQ ID NO:3): APSSSPME. A preferred second intervening spacer peptide (Linker 2) has the sequence is SEQ ID NO:4: GGGSGGGG. The preferred cysteine-containing third intervening spacer peptide (Linker 3) will contain 1, 2, 3 or more cysteines. A preferred cysteine-containing spacer peptide (Linker 3) has the sequence is SEQ ID NO:5: GGCGGG. A preferred fourth spacer peptide (Linker 4) has the sequence GGG or is SEQ ID NO:6: GGGNS.

Most preferably, the length of the intervening linker peptide (Linker 2, which separates such VL and VH Domains) is selected to substantially or completely prevent the VL and VH Domains of the polypeptide chain from binding to one another. Thus the VL and VH Domains of the first polypeptide chain are substantially or completely incapable of binding to one another. Likewise, the VL and VH Domains of the second polypeptide chain are substantially or completely incapable of binding to one another.

The heterodimer-promoting domains of the first and second polypeptides differ from one another and are designed to associate with one another so as to promote association of the first and second polypeptide chains. Thus, in a preferred embodiment, one of these polypeptide chains will be engineered to contain a heterodimer-promoting "E-coil" Domain (SEQ ID NO:7):

EVAALEKEVAALEKEVAALEKEVAALEK whose residues will form a negative charge at pH 7, while the other of the two polypeptide chains will be engineered to contain a heterodimer-promoting "K-coil" Domain (SEQ ID NO:8):

KVAALKEKVAALKEKVAALKEKVAALKE whose residues will form a positive charge at pH 7. The presence of such charged domains promotes association between the first and second polypeptides, and thus fosters heterodimerization. It is immaterial which coil is provided to which chain, as long as the coils employed on the first and second polypeptide chains differ so as to foster heterodimerization between such chains.

As indicated above, the CH2 and CH3 domains of the first and third polypeptides are preferably mutated to reduce (relative to a wild-type Fc region) or eliminate binding to FcγRIA (CD64), FcγRIIA (CD32A), FcγRIIB (CD32B), FcγRIIIA (CD16a) or FcγRIIIB (CD16b). Such mutations are well known in the art and include amino acid substitutions at positions 234 and 235, a substitution at position 265 or a substitution at position 297 (see, for example, U.S. Pat. No. 5,624,821, herein incorporated by reference). In a preferred embodiment the CH2 and CH3 domain includes a substitution at position 234 with alanine and 235 with alanine.

The CH2 and/or CH3 domains of the first and third polypeptides need not be identical, and advantageously are modified to foster complexing between the two polypeptides. For example, an amino acid substitution (preferably a substitution with an amino acid comprising a bulky side group forming a 'knob', e.g., tryptophan) can be introduced into the CH2 or CH3 domain such that steric interference will prevent interaction with a similarly mutated domain and will obligate the mutated domain to pair with a domain into which a complementary, or accommodating mutation has been engineered, i.e., 'the hole' (e.g., a substitution with glycine). Such sets of mutations can be engineered into any pair of polypeptides comprising the Fc diabody molecule, and further, engineered into any portion of the polypeptides chains of said pair. Methods of protein engineering to favor heterodimerization over homodimerization are well known in the art, in particular with respect to the engineering of immunoglobulin-like molecules, and are encompassed herein (see e.g., Ridgway et al. (1996) "'Knobs-Into-Holes' Engineering Of Antibody CH3 Domains For Heavy Chain Heterodimerization," Protein Engr. 9:617-621, Atwell et al. (1997) "Stable Heterodimers From Remodeling The Domain Interface Of A Homodimer Using A Phage Display Library," J. Mol. Biol. 270: 26-35, and Xie et al. (2005) "A New Format Of Bispecific Antibody: Highly Efficient Heterodimerization, Expression And Tumor Cell Lysis," J. Immunol. Methods 296:95-101; each of which is hereby incorporated herein by reference in its entirety). Preferably the 'knob' is engineered into the CH2-CH3 domains of the first polypeptide chain and the 'hole' is engineered into the CH2-CH3 domains of the third polypeptide chain. Thus, the 'knob' will help in preventing the first polypeptide chain from homodimerizing via its CH2 and/or CH3 domains. As the third polypeptide chain preferably contains the 'hole' substitution it will heterodimerize with the first polypeptide chain as well as homodimerize with itself. A preferred knob is created by modifying a native IgG Fc region to contain the modification T366W. A preferred hole is created by modifying a native IgG Fc region to contain the modification T366S, L368A and Y407V. To aid in purifying the third polypeptide chain homodimer from the final bi-specific monovalent Fc diabody comprising the first, second and third polypeptide chains, the protein A binding site of the CH2 and CH3 domains of the third polypeptide chain is preferably mutated by amino acid substitution at position 435 (H435R). To aid in purifying the third polypeptide chain homodimer from the final bi-specific monovalent Fc diabody comprising the first, second and third polypeptide chains, the protein A binding site of the CH2 and CH3 domains of the third polypeptide chain is preferably mutated by amino acid substitution. Thus the third polypeptide chain homodimer will not bind to protein A, whereas the bi-specific monovalent Fc diabody will retain its ability to bind protein A via the protein A binding site on the first polypeptide chain.

A preferred sequence for the CH2 and CH3 domains of an antibody Fc region present in the first polypeptide chain is (SEQ ID NO:9):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGK
```

A preferred sequence for the CH2 and CH3 domains of an antibody Fc region present in the third polypeptide chain is (SEQ ID NO:10):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGK
```

A preferred sequence for the VL Domain of an antibody that binds CD32B (VL$_{CD32B}$) is (SEQ ID NO:11):

```
DIQMTQSPSS LSASVGDRVT ITCRASQEIS GYLSWLQQKP
GKAPRRLIYA ASTLDSGVPS RFSGSESGTE FTLTISSLQP
EDFATYYCLQ YFSYPLTFGG GTKVEIK
```

A preferred sequence for the VH Domain of an antibody that binds CD32B (VH$_{CD32B}$) is (SEQ ID NO:12):

```
EVQLVESGGG LVQPGGSLRL SCAASGFTFS DAWMDWVRQA
PGKGLEWVAE IRNKAKNHAT YYAESVIGRF TISRDDAKNS
LYLQMNSLRA EDTAVYYCGA LGLDYWGQGT LVTVSS
```

A preferred sequence for the VL Domain of an antibody that binds CD79b

```
DVVMTQSPLS LPVTLGQPAS ISCKSSQSLL DSDGKTYLNW
FQQRPGQSPN RLIYLVSKLD SGVPDRFSGS GSGTDFTLKI
SRVEAEDVGV YYCWQGTHFP LTFGGGTKLE IK
```

A preferred sequence for the VH Domain of an antibody that binds CD79b (VH$_{CD79b}$) is (SEQ ID NO:14):

```
QVQLVQSGAE VKKPGASVKV SCKASGYTFT SYWMNWVRQA
PGQGLEWIGM IDPSDSETHY NQKFKDRVTM TTDTSTSTAY
MELRSLRSDD TAVYYCARAM GYWGQGTTVT VSS
```

Thus, a preferred sequence for the first polypeptide chain has the structure, in the N-terminal to C-terminal direction, of: Peptide 1, a CH2-CH3 domain of an IgG Fc region, Linker 1, a VL Domain of an antibody that binds CD32B (VL$_{CD32B}$), Linker 2, a VH Domain of an antibody that binds CD79b (VH$_{CD79b}$), Linker 3, an E-coil Domain, a Linker 4 and a C-terminus. The amino acid sequence of such a preferred polypeptide is (SEQ ID NO:15):

```
DKTHTCPPCP APEAAGGPSV FLFPPKPKDT LMISRTPEVT
CVVVDVSHED PEVKFNWYVD GVEVHNAKTK PREEQYNSTY
RVVSVLTVLH QDWLNGKEYK CKVSNKALPA PIEKTISKAK
GQPREPQVYT LPPSREEMTK NQVSLWCLVK GFYPSDIAVE
WESNGQPENN YKTTPPVLDS DGSFFLYSKL TVDKSRWQQG
NVFSCSVMHE ALHNHYTQKS LSLSPGKAPS SSPMEDIQMT
QSPSSLSASV GDRVTITCRA SQEISGYLSW LQQKPGKAPR
RLIYAASTLD SGVPSRFSGS ESGTEFTLTI SSLQPEDFAT
YYCLQYFSYP LTFGGGTKVE IKGGGSGGGG QVQLVQSGAE
VKKPGASVKV SCKASGYTFT SYWMNWVRQA PGQGLEWIGM
IDPSDSETHY NQKFKDRVTM TTDTSTSTAY MELRSLRSDD
TAVYYCARAM GYWGQGTTVT VSSGCGGGE VAALEKEVAA
LEKEVAALEK EVAALEKGGG NS
```

In SEQ ID NO:15, amino acid residues 1-10 are Peptide 1 (SEQ ID NO:1), amino acid residues 11-227 are the CH2 and CH3 domains of an IgG antibody Fc region (SEQ ID NO:9), amino acid residues 228-235 are Linker 1 (SEQ ID NO:3), amino acid residues 236-342 is the VL Domain of an antibody that binds CD32B (VL$_{CD32B}$) (SEQ ID NO:11), amino acid residues 343-350 are Linker 2 (SEQ ID NO:4), amino acid residues 351-463 is the VH Domain of an antibody that binds CD79b (VH$_{CD79b}$) (SEQ ID NO:14), amino acid residues 464-469 are Linker 3 (SEQ ID NO:5), amino acid residues 470-497 are the heterodimer-promoting E-coil Domain (SEQ ID NO:7), and amino acid residues 498-502 are Linker 4 (SEQ ID NO:6).

A preferred polynucleotide that encodes the first polypeptide chain has the sequence (SEQ ID NO:23):

```
gacaaaactcacacatgcccaccgtgcccagcacctgaagccgcgggggg
accgtcagtcttcctcttccccccaaaacccaaggacaccctcatgatct
cccggacccctgaggtcacatgcgtggtggtggacgtgagccacgaagac
cctgaggtcaagttcaactggtacgtggacggcgtggaggtgcataatgc
caagacaaagccgcgggaggagcagtacaacagcacgtaccgtgtggtca
gcgtcctcaccgtcctgcaccaggactggctgaatggcaaggagtacaag
tgcaaggtctccaacaaagcccctcccagccccatcgagaaaaccatctc
caaagccaaagggcagccccgagaaccacaggtgtacaccctgcccccat
cccgggaggagatgaccaagaaccaggtcagcctgtggtgcctggtcaaa
ggcttctatcccagcgacatcgccgtggagtgggagagcaatgggcagcc
ggagaacaactacaagaccacgcctcccgtgctggactccgacggctcct
tcttcctctacagcaagctcaccgtggacaagagcaggtggcagcagggg
aacgtcttctcatgctccgtgatgcatgaggctctgcacaaccactacac
gcagaagagcctctccctgtctccgggtaaagccccttccagctcccta
tggaagacatccagatgacccagtctccatcctccttatctgcctctgtg
ggagatagagtcaccatcacttgtcgggcaagtcaggaaattagtggtta
cttaagctggctgcagcagaaaccaggcaaggcccctagacgcctgatct
acgccgcatccactttagattctggtgtcccatccaggttcagtggcagt
gagtctgggaccgagttcaccctcaccatcagcagccttcagcctgaaga
ttttgcaacctattactgtctacaatattttagttatccgctcacgttcg
ggggggggaccaaggtggaaataaaaggaggcggatccggcggcggaggc
caggttcagctggtgcagtctggagctgaggtgaagaagcctggcgcctc
agtgaaggtctcctgcaaggcttctggttacacctttaccagctactgga
tgaactgggtgcgacaggcccctggacaagggcttgagtggatcggaatg
attgatccttcagacagtgaaactcactacaatcaaaagttcaaggacag
agtcaccatgaccacagacacatccacgagcacagcctacatggagctga
ggagcctgagatctgacgacacggccgtgtattactgtgcgagagctatg
ggctactggggccaagggaccacggtcaccgtctcctcggaggatgtgg
cggtggagaagtggccgcactggagaaagaggttgctgctttggagaagg
aggtcgctgcacttgaaaaggaggtcgcagccctggagaaaggcggcggg
aactct
```

A preferred sequence for the second polypeptide chain is (SEQ ID NO:16):

```
DVVMTQSPLS LPVTLGQPAS ISCKSSQSLL DSDGKTYLNW

FQQRPGQSPN RLIYLVSKLD SGVPDRFSGS GSGTDFTLKI

SRVEAEDVGV YYCWQGTHFP LTFGGGTKLE IKGGGSGGGG

EVQLVESGGG LVQPGGSLRL SCAASGFTFS DAWMDWVRQA

PGKGLEWVAE IRNKAKNHAT YYAESVIGRF TISRDDAKNS

LYLQMNSLRA EDTAVYYCGA LGLDYWGQGT LVTVSSGGCG

GGKVAALKEK VAALKEKVAA LKEKVAALKE
```

In SEQ ID NO:16, amino acid residues 1-112 is the VL Domain of an antibody that binds CD79b (VL$_{CD79b}$) (SEQ ID NO:13), amino acid residues 113-120 are Linker 2 (SEQ ID NO:4), amino acid residues 121-236 is the VH Domain of an antibody that binds CD32B (VH$_{CD32B}$) (SEQ ID NO:12), amino acid residues 237-242 are Linker 3 (SEQ ID NO:5), and amino acid residues 243-270 are the heterodimer-promoting K-coil Domain (SEQ ID NO:8).

A preferred polynucleotide that encodes the second polypeptide chain has the sequence (SEQ ID NO:24):

```
gatgttgtgatgactcagtctccactctccctgcccgtcacccttggaca gccggcctccatctcctgcaagtcaagtcagagcctcttagatagtgatg gaaagacatatttgaattggtttcagcagaggccaggccaatctccaaac cgcctaatttatctggtgtctaaactggactctgggtcccagacagatt cagcggcagtgggtcaggcactgatttcacactgaaaatcagcagggtgg aggctgaggatgttggggtttattactgctggcaaggtacacattttccg ctcacgttcggcggagggaccaagcttgagatcaaaggaggcggatccgg cggcggaggcgaagtgcagcttgtggagtctggaggaggcttggtgcaac ctggaggatccctgagactctcttgtgccgcctctggattcactttagt gacgcctggatggactgggtccgtcaggcccaggcaaggggcttgagtg ggttgctgaaattagaaacaaagctaaaaatcatgcaacatactatgctg agtctgtgatagggaggttcaccatctcaagagatgacgccaaaacagt ctgtacctgcaaatgaacagcttaagagctgaagacactgccgtgtatta ctgtggggctctgggccttgactactgggccaaggcaccctggtgaccg tctcctccggaggatgtggcggtggaaaagtggccgcactgaaggagaaa gttgctgctttgaaagagaaggtcgccgcacttaaggaaaaggtcgcagc cctgaaagag
```

A preferred sequence for the third polypeptide chain is SEQ ID NO:17:

```
DKTHTCPPCP APEAAGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALPA PIEKTISKAK

GQPREPQVYT LPPSREEMTK NQVSLSCAVK GFYPSDIAVE

WESNGQPENN YKTTPPVLDS DGSFFLVSKL TVDKSRWQQG

NVFSCSVMHE ALHNRYTQKS LSLSPGK
```

In SEQ ID NO:17, amino acid residues 1-10 are Peptide 1 (SEQ ID NO:1), and amino acid residues 11-227 are the CH2 and CH3 domains of an IgG antibody Fc region (SEQ ID NO:10).

A preferred polynucleotide that encodes the third polypeptide chain has the sequence (SEQ ID NO:25):

```
gacaaaactcacacatgcccaccgtgcccagcacctgaagccgcggggg gaccgtcagtcttcctcttcccccaaaacccaaggacaccctcatgat ctcccggacccctgaggtcacatgcgtggtggtggacgtgagccacgaa gaccctgaggtcaagttcaactggtacgtggacggcgtggaggtgcata atgccaagacaaagccgcgggaggagcagtacaacagcacgtaccgtgt ggtcagcgtcctcaccgtcctgcaccaggactggctgaatggcaaggag tacaagtgcaaggtctccaacaaagccctcccagcccccatcgagaaaa ccatctccaaagccaaagggcagccccgagaaccacaggtgtacaccct gcccccatcccgggaggagatgaccaagaaccaggtcagcctgagttgc gcagtcaaaggcttctatcccagcgacatcgccgtggagtgggagagca atgggcagccggagaacaactacaagaccacgcctcccgtgctggactc cgacggctccttcttcctcgtcagcaagctcaccgtggacaagagcagg tggcagcaggggaacgtcttctcatgctccgtgatgcatgaggctctgc acaaccgctacacgcagaagagcctctccctgtctccgggtaaa
```

As disclosed in WO 2012/018687, in order to improve the in vivo pharmacokinetic properties of diabody molecules, the molecules may be modified to contain a polypeptide portion of a serum-binding protein at one or more of the termini of the diabody molecule. Most preferably, such polypeptide portion of a serum-binding protein will be installed at the C-terminus of the diabody molecule. A particularly preferred polypeptide portion of a serum-binding protein for this purpose is the Albumin-Binding Domain (ABD) from streptococcal protein G. The Albumin-Binding Domain 3 (ABD3) of protein G of *Streptococcus* strain G148 is particularly preferred.

The Albumin-Binding Domain 3 (ABD3) of protein G of *Streptococcus* strain G148 consists of 46 amino acid residues forming a stable three-helix bundle and has broad albumin binding specificity (Johansson, M. U. et al. (2002) "*Structure, Specificity, And Mode Of Interaction For Bacterial Albumin-Binding Modules,*" J. Biol. Chem. 277(10): 8114-8120). Albumin is the most abundant protein in plasma and has a half-life of 19 days in humans. Albumin possesses several small molecule binding sites that permit it to non-covalently bind to other proteins and thereby extend their serum half-lives. Preferably, a short linker (Linker 5) (such as GGGS (SEQ ID NO:18) or GGGNS (SEQ ID NO:6) is employed to separate the E-coil (or K-coil) of such polypeptide chain from the Albumin-Binding Domain. A preferred Albumin-Binding Domain (ABD) has the amino acid sequence (SEQ ID NO:19):

```
LAEAKVLANR ELDKYGVSDY YKNLIDNAKS AEGVKALID
EILAALP
```

II. Alternative CD32B×CD79b Fc Diabodies of the Present Invention

Figure 2:
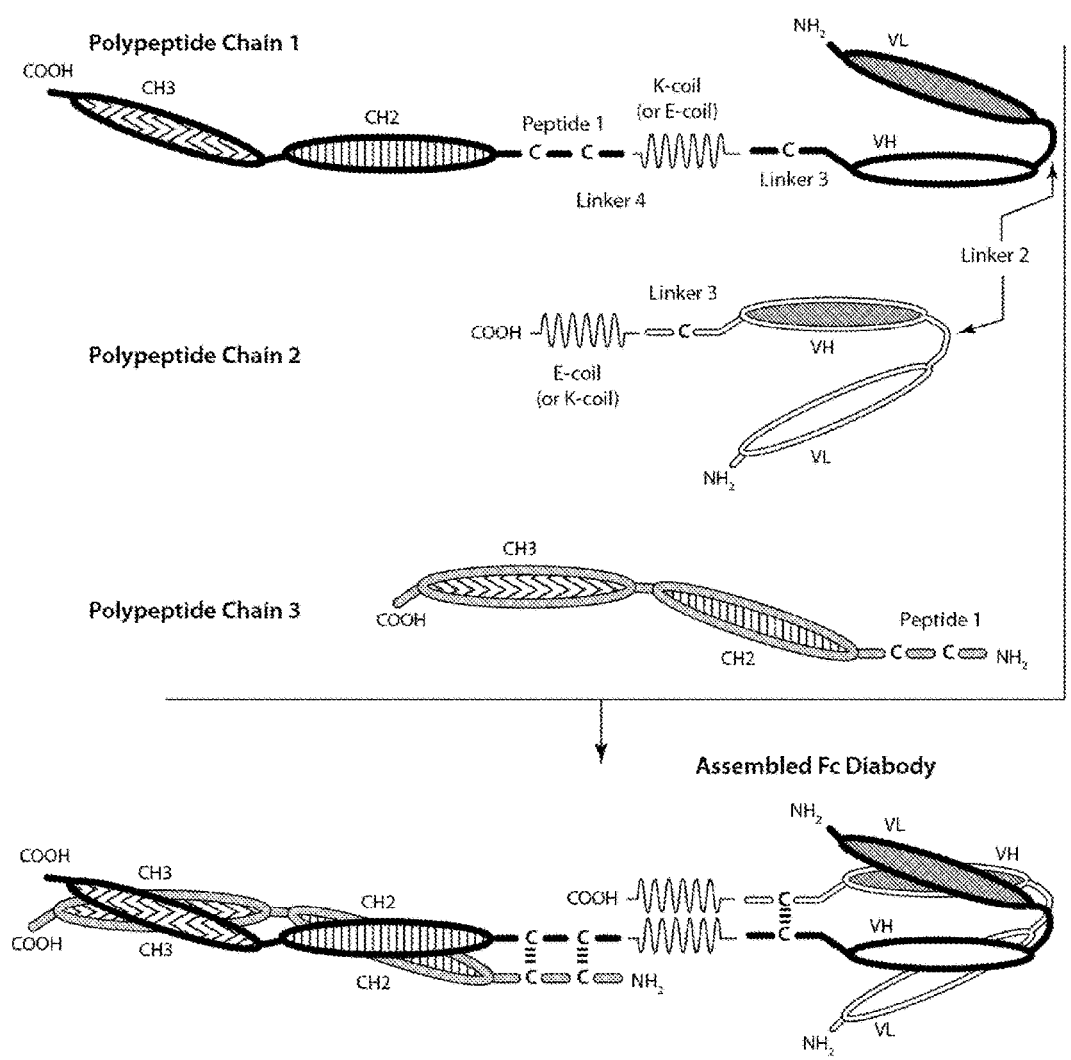
FIG. 2 illustrates the three polypeptide chains of an alternative bi-specific monovalent Fc diabody and the structure of the covalently associated chains.

An alternative CD32B×CD79b bi-specific monovalent Fc diabody molecule of the present invention is shown schematically in FIG. 2. Such alternative CD32B×CD79b Fc diabody molecules possess three polypeptide chains, of which the first and second polypeptide chains are covalently bonded to one another and the first and third polypeptide chains are bonded to one another. The alternative CD32B×CD79b bi-specific monovalent Fc diabody molecules differ in the order of its domains relative to the order present in the preferred CD32B×CD79b bi-specific monovalent Fc diabody molecules. However, as in the case of the preferred CD32B×CD79b Fc diabody, the VL Domain of the first polypeptide chain of the alternative CD32B×CD79b bi-specific monovalent Fc diabody interacts with the VH Domain of the second polypeptide chain of the alternative CD32B×CD79b bi-specific monovalent Fc diabody in order to form a first functional antigen binding site that is specific for the first antigen (i.e., either CD32B or CD79b). Likewise, the VL Domain of the second polypeptide chain of the alternative CD32B×CD79b bi-specific monovalent Fc diabody interacts with the VH Domain of the first polypeptide chain of the alternative CD32B×CD79b bi-specific monovalent Fc diabody in order to form a second functional antigen binding site that is specific for the second antigen (i.e., either CD79b or CD32B, depending upon the identity of the first antigen). Thus, the selection of the VL and VH Domains of the first and second polypeptide chains are coordinated, such that the two polypeptide chains collectively comprise VL and VH Domains capable of binding to CD32B and CD79b (i.e., they comprise $VL_{CD32B}/VH_{CD32B}$ and $VL_{CD79b}/VH_{CD79b}$) (FIG. 2). Collectively, each such VL and VH Domain, and the intervening Linker that separates them, are referred to as an Antigen-Binding Domain of the molecule.

The first polypeptide chain of such alternative CD32B×CD79b Fc diabody comprises, in the N-terminal to C-terminal direction, an amino terminus, the VL Domain of a monoclonal antibody capable of binding to either CD32B or CD79b (i.e., either $VL_{CD32B}$ or $VL_{CD79b}$), an intervening spacer peptide (Linker 2), a VH Domain of a monoclonal antibody capable of binding to either CD79b (if such first polypeptide chain contains $VL_{CD32B}$) or CD32B (if such first polypeptide chain contains $VL_{CD79b}$), a cysteine-containing third intervening spacer peptide (Linker 3), a heterodimer-promoting domain, an optional fourth spacer peptide (Linker 4) to provide improved stabilization to the heterodimer-promoting domain (preferably an E-coil Domain), a cysteine-containing peptide (Peptide 1), an IgG Fc Domain (preferably, the CH2 and CH3 domains of an antibody Fc region, and a C-terminus. Preferably, the Fc Domain of the first polypeptide chain will cause reduced binding to FcγRIA (CD64), FcγRIIA (CD32A), FcγRIIB (CD32B), FcγRIIIA (CD16a) or FcγRIIIB (CD16b) (relative to the binding exhibited by a wild-type Fc region) or will substantially eliminate the ability of such Fc Domain to bind to such receptor(s) (FIG. 2).

The second polypeptide chain of such alternative CD32B×CD79b Fc diabody comprises, in the N-terminal to C-terminal direction, an amino terminus, a VL Domain of a monoclonal antibody capable of binding to either CD79b or CD32B (i.e., either $VL_{CD79b}$ or $VL_{CD32B}$, depending upon the VL Domain selected for the first polypeptide chain of the diabody), an intervening linker peptide (Linker 2), a VH Domain of a monoclonal antibody capable of binding to either CD32B (if such second polypeptide chain contains $VL_{CD79b}$) or CD32B (if such second polypeptide chain contains $VL_{CD32B}$), a cysteine-containing spacer peptide (Linker 3), a heterodimer-promoting domain (preferably a K-coil Domain), and a C-terminus (FIG. 2).

The third polypeptide chain of the preferred CD32B×CD79b Fc diabody comprises, in the N-terminal to C-terminal direction, an amino terminus, a cysteine-containing peptide (Peptide 1), an IgG Fc Domain (preferably, the CH2 and CH3 domains of an antibody Fc region) having the same isotype as that of the Fc Domain of the first polypeptide chain and a C-terminus. Preferably, the Fc Domain of the third polypeptide chain will cause reduced binding to FcγRIA (CD64), FcγRIIA (CD32A), FcγRIIB (CD32B), FcγRIIIA (CD16a) or FcγRIIIB (CD16b) (relative to the binding exhibited by a wild-type Fc region) or will substantially eliminate the ability of such Fc Domain to bind to such receptor(s) (FIG. 2).

III. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of the CD32B×CD79b Fc diabodies of the present invention, and in particular any of the CD32B×CD79b Fc diabodies disclosed herein or a combination of such agents and a pharmaceutically acceptable carrier. Preferably, compositions of the invention comprise a prophylactically or therapeutically effective amount of one or more molecules of the invention and a pharmaceutically acceptable carrier.

The invention also encompasses pharmaceutical compositions comprising such CD32B×CD79b Fc diabodies and a second therapeutic antibody (e.g., autoimmune or inflammatory disease antigen specific monoclonal antibody) that is specific for a particular autoimmune or inflammatory disease antigen, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with such disclosed CD32B×CD79b Fc diabodies alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more molecules of the invention. In another embodiment, a kit further comprises one or more other prophylactic or therapeutic agents useful for the treatment of an autoimmune or inflammatory disease, in one or more containers. In another embodiment, a kit further comprises one or more antibodies that bind one or more autoimmune or inflammatory disease antigens associated with autoimmune or inflammatory disease. In certain embodiments, the other prophylactic or therapeutic agent is a chemotherapeutic. In other embodiments, the prophylactic or therapeutic agent is a biological or hormonal therapeutic.

IV. Uses of the Compositions of the Invention

The CD32B×CD79b Fc diabodies of the present invention have the ability to treat any disease or condition associated with or characterized by the expression of CD79b or having a B cell component to the disease. Thus, without limitation, pharmaceutical compositions comprising such molecules may be employed in the diagnosis or treatment of autoimmune or inflammatory diseases or conditions.

Thus, the invention may be used to treat, prevent, slow the progression of, and/or ameliorate a symptom of B cell mediated diseases or disorders, including graft rejection, graft-versus-host disease (GvHD) and systemic lupus erythematosis (SLE).

V. Methods of Administration

The compositions of the present invention may be provided for the treatment, prophylaxis, and amelioration of one or more symptoms associated with a disease, disorder or infection by administering to a subject an effective amount of a pharmaceutical composition of the invention. In a preferred aspect, such compositions are substantially purified (i.e., substantially free from substances that limit its effect or produce undesired side-effects). In a specific embodiment, the subject is an animal, preferably a mammal such as non-primate (e.g., bovine, equine, feline, canine, rodent, etc.) or a primate (e.g., monkey such as, a cynomolgous monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) *"Receptor-Mediated In Vitro Gene Transformation By A Soluble DNA Carrier System,"* J. Biol. Chem. 262: 4429-4432), construction of a nucleic acid as part of a retroviral or other vector, etc.

Methods of administering a bi-specific monovalent Fc diabody of the invention include, but are not limited to, parenteral administration (e.g., intradermal, intramuscular, intraperitoneal, intravenous and subcutaneous), epidural, and mucosal (e.g., intranasal and oral routes). In a specific embodiment, the molecules of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the CD32B×CD79b Fc diabodies of the invention are packaged in a hermetically sealed container such as an ampoule or sachette indicating the quantity of such molecules. In one embodiment, the CD32B×CD79b Fc diabodies of the invention are supplied as a dry sterilized lyophilized powder or water free concentrate in a hermetically sealed container and can be reconstituted, e.g., with water or saline to the appropriate concentration for administration to a subject. Preferably, the CD32B×CD79b Fc diabodies of the invention are supplied as a dry sterile lyophilized powder in a hermetically sealed container at a unit dosage of at least 5 µg, more preferably at least 10 µg, at least 15 µg, at least 25 µg, at least 50 µg, at least 100 µg, or at least 200 µg.

The lyophilized CD32B×CD79b Fc diabodies of the invention should be stored at between 2 and 8° C. in their original container and the molecules should be administered within 12 hours, preferably within 6 hours, within 5 hours, within 3 hours, or within 1 hour after being reconstituted. In an alternative embodiment, the CD32B×CD79b Fc diabodies of the invention are supplied in liquid form in a hermetically sealed container indicating the quantity and concentration of the molecule, fusion protein, or conjugated molecule. Preferably, the liquid form of the CD32B×CD79b Fc diabodies of the invention is supplied in a hermetically sealed container in which the molecules are present at a concentration of least 1 µg/ml, more preferably at least 2.5 µg/ml, at least 5 µg/ml, at least 10 µg/ml, at least 50 µg/ml, or at least 100 µg/ml.

The amount of the CD32B×CD79b Fc diabodies of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For CD32B×CD79b Fc diabodies Fc diabodies encompassed by the invention, the dosage administered to a patient is typically at least about 0.01 µg/kg, at least about 0.05 µg/kg, at least about 0.1 µg/kg, at least about 0.2 µg/kg, at least about 0.5 µg/kg, at least about 1 µg/kg, at least about 2 µg/kg, at least about 5 µg/kg, at least about 10 µg/kg, at least about 20 µg/kg, at least about 50 µg/kg, at least about 0.1 mg/kg, at least about 1 mg/kg, at least about 5 mg/kg, at least about 10 mg/kg, at least about 30 mg/kg, at least about 50 mg/kg, at least about 75 mg/kg, at least about 100 mg/kg, at least about 125 mg/kg, at least about 150 mg/kg or more of the subject's body weight.

The dosage and frequency of administration of the bi-specific monovalent Fc diabodies of the invention may be reduced or altered by enhancing uptake and tissue penetration of the bi-specific monovalent Fc diabodies by modifications such as, for example, lipidation.

In one embodiment, the dosage of the CD32B×CD79b Fc diabodies of the invention administered to a patient may be calculated for use as a single agent therapy. In another embodiment the bi-specific monovalent Fc diabodies of the invention are used in combination with other therapeutic compositions and the dosage administered to a patient are lower than when such bi-specific monovalent Fc diabody molecules are used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

In another embodiment, the compositions can be delivered in a vesicle, in particular a liposome (See Langer (1990) "New Methods Of Drug Delivery," Science 249:1527-1533); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 3 17-327; see generally ibid.).

In yet another embodiment, the compositions can be delivered in a controlled-release or sustained-release system. Any technique known to one of skill in the art can be used to produce sustained-release formulations comprising one or more molecules of the invention. See, e.g., U.S. Pat. No. 4,526,938; PCT publication WO 91/05548; PCT publication WO 96/20698; Ning et al. (1996) "Intratumoral Radioimmunotheraphy Of A Human Colon Cancer Xenograft Using A Sustained-Release Gel," Radiotherapy & Oncology 39:179-189, Song et al. (1995) "Antibody Mediated Lung Targeting Of Long-Circulating Emulsions," PDA Journal of Pharmaceutical Science & Technology 50:372-397; Cleek et al. (1997) "Biodegradable Polymeric Carriers For A bFGF Antibody For Cardiovascular Application," Pro. Int'l. Symp. Control. Rel. Bioact. Mater. 24:853-854; and Lam et al. (1997) "Microencapsulation Of Recombinant Humanized Monoclonal Antibody For Local Delivery," Proc. Int'l. Symp. Control Rel. Bioact. Mater. 24:759-760, each of which is incorporated herein by reference in its entirety. In one embodiment, a pump may be used in a controlled-release system (See Langer, supra; Sefton, (1987) "Implantable Pumps," CRC Crit. Rev. Biomed. Eng. 14:201-240; Buchwald et al. (1980) "Long-Term, Continuous Intravenous Heparin Administration By An Implantable Infusion Pump In Ambulatory Patients With Recurrent Venous Thrombosis," Surgery 88:507-516; and Saudek et al. (1989) "A Preliminary Trial Of The Programmable Implantable Medication System For Insulin Delivery," N. Engl. J. Med. 321:574-579). In another embodiment, polymeric materials can be used to achieve controlled release of antibodies (see e.g., MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Levy et al. (1985) "Inhibition Of Calcification Of Bioprosthetic Heart Valves By Local Controlled-Release Diphosphonate," Science 228:190-192; During et al. (1989) "Controlled Release Of Dopamine From A Polymeric Brain Implant: In Vivo Characterization," Ann. Neurol. 25:351-356; Howard et al. (1989) "Intracerebral Drug Delivery In Rats With Lesion-Induced Memory Deficits," J. Neurosurg. 7(1):105-112); U.S. Pat. Nos. 5,679,377; 5,916,597; 5,912, 015; 5,989,463; 5,128,326; PCT Publication No. WO 99/15154; and PCT Publication No. WO 99/20253). Examples of polymers used in sustained-release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled-release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). In another embodiment, polymeric compositions useful as controlled-release implants are used according to Dunn et al. (See U.S. Pat. No. 5,945,155). This particular method is based upon the therapeutic effect of the in situ controlled-release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled-release systems are discussed in the review by Langer (1990, "New Methods Of Drug Delivery," Science 249:1527-1533). Any technique known to one of skill in the art can be used to produce sustained-release formulations comprising one or more therapeutic agents of the invention. See, e.g., U.S. Pat. No. 4,526,938; International Publication Nos. WO 91/05548 and WO 96/20698; Ning et al. (1996) "Intratumoral Radioimmunotheraphy Of A Human Colon Cancer Xenograft Using A Sustained-Release Gel," Radiotherapy & Oncology 39:179-189, Song et al. (1995) "Antibody Mediated Lung Targeting Of Long-Circulating Emulsions," PDA Journal of Pharmaceutical Science & Technology 50:372-397; Cleek et al. (1997) "Biodegradable Polymeric Carriers For A bFGF Antibody For Cardiovascular Application," Pro. Int'l. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety.

In a specific embodiment where the composition of the invention is a nucleic acid encoding a bi-specific monovalent Fc diabody of the invention, the nucleic acid can be administered in vivo to promote expression of its encoded bi-specific monovalent Fc diabody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al. (1991) "*Antennapedia Homeobox Peptide Regulates Neural Morphogenesis*," Proc. Natl. Acad. Sci. (U.S.A.) 88:1864-1868), etc. Alternatively, a nucleic acid can be introduced intracellularly and incorporated within host cell DNA for expression by homologous recombination.

Treatment of a subject with a therapeutically or prophylactically effective amount of the CD32B×CD79b Fc diabodies of the invention can include a single treatment or, preferably, can include a series of treatments. In a preferred example, a subject is treated with molecules of the invention one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the molecules used for treatment may increase or decrease over the course of a particular treatment.

Having now generally described the invention, the same will be more readily understood through reference to the following examples, which are provided by way of illustration and are not intended to be limiting of the present invention unless specified.

Example 1

Construction of CD32B×CD79b Bi-Specific Monovalent Fc Diabodies and Control Diabodies Table 1 contains a list of sequences of the polypeptide chains of the preferred CD32B×CD79b Fc diabody that were expressed and purified. Additionally, two control diabodies were produced: one bi-specific monovalent for CD32B and FITC and the second bi-specific monovalent for CD79b and FITC.

TABLE 1

| Preferred CD32B × CD79b Bi-specific Fc Diabody | Substituent Polypeptides (in the N-Terminal to C-Terminal Direction) |
|---|---|
| First Polypeptide Chain (SEQ ID NO: 15) | SEQ ID NO: 1 |
| | SEQ ID NO: 9 |
| | SEQ ID NO: 3 |

TABLE 1-continued

| Preferred CD32B × CD79b Bi-specific Fc Diabody | Substituent Polypeptides (in the N-Terminal to C-Terminal Direction) |
|---|---|
| | SEQ ID NO: 11 |
| | SEQ ID NO: 4 |
| | SEQ ID NO: 14 |
| | SEQ ID NO: 5 |
| | SEQ ID NO: 7 |
| | SEQ ID NO: 6 |
| Second Polypeptide Chain (SEQ ID NO: 16) | SEQ ID NO: 13 |
| | SEQ ID NO: 4 |
| | SEQ ID NO: 12 |
| | SEQ ID NO: 5 |
| | SEQ ID NO: 8 |
| Third Polypeptide Chain (SEQ ID NO: 17) | SEQ ID NO: 1 |
| | SEQ ID NO: 10 |

The above-described CD32B×CD79b Fc diabody was found to be capable of simultaneously binding to CD32B and to CD79b. The control CD32B×FITC diabody was found to be capable of simultaneously binding to CD32B and to FITC. The control CD79b×FITC diabody was found to be capable of simultaneously binding to CD79b and to FITC. The CD32B×CD79b Fc diabody is a heterotrimer composed of three polypeptide chains (one chain of each recited amino acid sequence). Methods for forming bi-specific monovalent diabodies are provided in WO 2006/113665, WO 2008/157379, WO 2010/080538, WO 2012/018687, WO 2012/162068 and WO 2012/162067.

In order to further demonstrate the advantages of such preferred CD32B×CD79b Fc diabody, two non-Fc containing CD32B×CD79b diabodies were also prepared. These diabodies are each composed of two polypeptide chains, and differ in that one of the diabodies (the CD32B×CD79b (ABD) diabody) contains an Albumin-Binding Domain, whereas the other (the CD32B×CD79b diabody) does not:

CD32B×CD79b (ABD) Diabody

The CD32B×CD79b (ABD) diabody is formed from a first polypeptide chain that comprises, in the N-terminal to C-terminal direction, the VL Domain of an antibody that binds CD32B (VL$_{CD32B}$), Linker 2, the VH Domain of an antibody that binds CD79b (VH$_{CD79b}$), Linker 3, the E-coil Domain, Linker 5, an Albumin-Binding Domain and a C-terminus. The second polypeptide chain comprises, in the N-terminal to C-terminal direction, the VL Domain of an antibody that binds CD79b (VL$_{CD79b}$), Linker 2, the VH Domain of an antibody that binds CD32B (VH$_{CD32B}$), Linker 3, the K-coil Domain and a C-terminus. The amino acid sequences of such polypeptides are as follows:

```
Amino Acid Sequence of First Polypeptide Chain
(SEQ ID NO: 20):
DIQMTQSPSS LSASVGDRVT ITCRASQEIS GYLSWLQQKP

GKAPRRLIYA ASTLDSGVPS RFSGSESGTE FTLTISSLQP

EDFATYYCLQ YFSYPLTFGG GTKVEIKGGG SGGGGQVQLV

QSGAEVKKPG ASVKVSCKAS GYTFTSYWMN WVRQAPGQGL

EWIGMIDPSD SETHYNQKFK DRVTMTTDTS TSTAYMELRS

LRSDDTAVYY CARAMGYWGQ GTTVTVSSGG CGGGEVAALE

KEVAALEKEV AALEKEVAAL EKGGGSLAEA KVLANRELDK

YGVSDYYKNL IDNAKSAEGV KALIDEILAA LP

Amino Acid Sequence of Second Polypeptide Chain
```

-continued (SEQ ID NO: 21):

```
DVVMTQSPLS LPVTLGQPAS ISCKSSQSLL DSDGKTYLNW

FQQRPGQSPN RLIYLVSKLD SGVPDRFSGS GSGTDFTLKI

SRVEAEDVGV YYCWQGTHFP LTFGGGTKLE IKGGGSGGGG

EVQLVESGGG LVQPGGSLRL SCAASGFTFS DAWMDWVRQA

PGKGLEWVAE IRNKAKNHAT YYAESVIGRF TISRDDAKNS

LYLQMNSLRA EDTAVYYCGA LGLDYWGQGT LVTVSSGGCG

GGKVAALKEK VAALKEKVAA LKEKVAALKE
```

CD32B×CD79b Diabody

The CD32B×CD79b diabody differs from the CD32B× CD79b (ABD) diabody in not having an Albumin-Binding Domain. Thus, such diabody is formed from a first polypeptide chain that comprises, in the N-terminal to C-terminal direction, the VL Domain of an antibody that binds CD32B (VL$_{CD32B}$), Linker 2, the VH Domain of an antibody that binds CD79b (VH$_{CD79b}$), Linker 3, the E-coil Domain, and a C-terminus. The second polypeptide chain comprises, in the N-terminal to C-terminal direction, the VL Domain of an antibody that binds CD79b (VL$_{CD79b}$), Linker 2, the VH Domain of an antibody that binds CD32B (VH$_{CD32B}$), Linker 3, the K-coil Domain and a C-terminus. The amino acid sequence of the first such first polypeptide chain of this diabody is (SEQ ID NO:22):

```
DIQMTQSPSS LSASVGDRVT ITCRASQEIS GYLSWLQQKP

GKAPRRLIYA ASTLDSGVPS RFSGSESGTE FTLTISSLQP

EDFATYYCLQ YFSYPLTFGG GTKVEIKGGG SGGGGQVQLV

QSGAEVKKPG ASVKVSCKAS GYTFTSYWMN WVRQAPGQGL

EWIGMIDPSD SETHYNQKFK DRVTMTTDTS TSTAYMELRS

LRSDDTAVYY CARAMGYWGQ GTTVTVSSGG CGGGEVAALE

KEVAALEKEV AALEKEVAAL EK
```

The amino acid sequence of the second polypeptide chain of this diabody is (SEQ ID NO:21, which is presented above.

Example 2

Figure 3A:
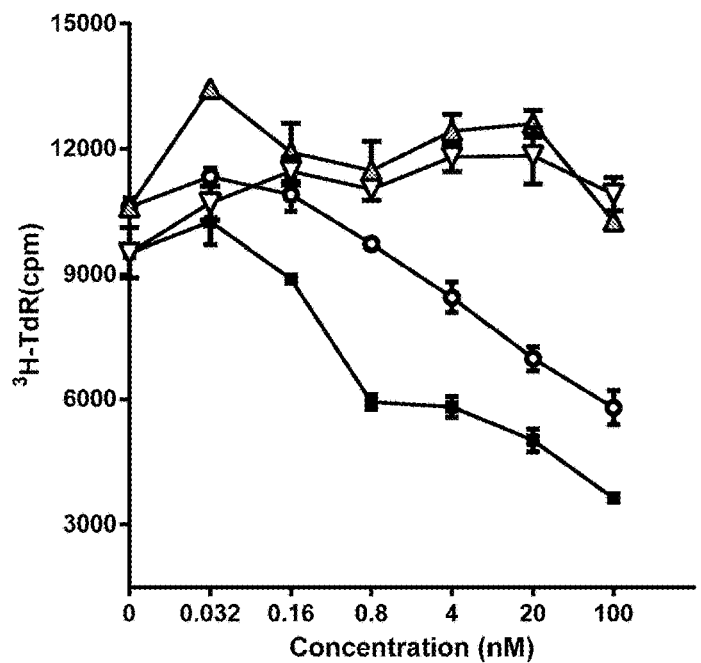
FIGS. 3A-3B show the ability of the preferred CD32B×CD79b Fc diabody and a non-Fc CD32B×CD79b (ABD) diabody to inhibit the proliferation of primary human B cells.
Figure 3B:
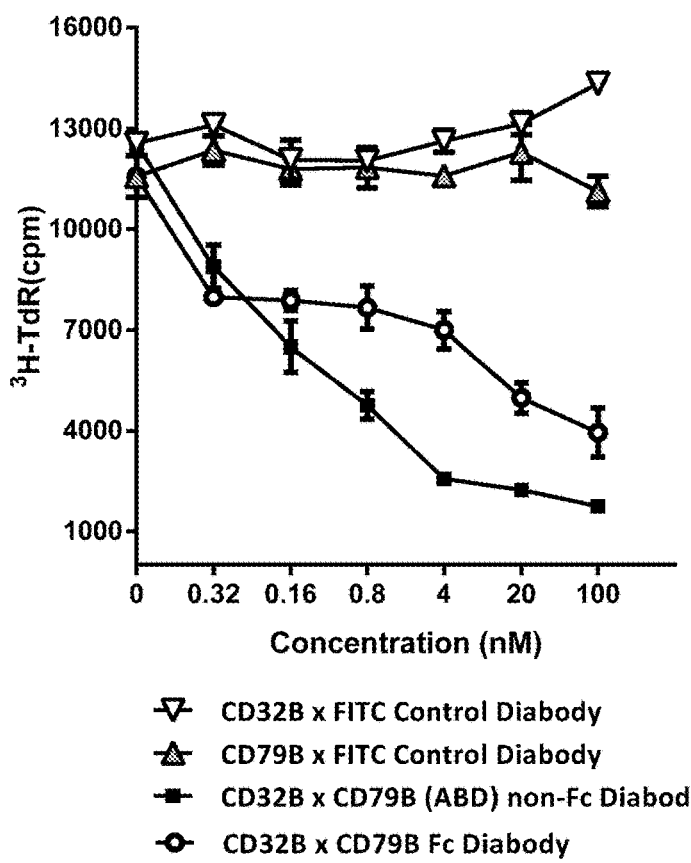

CD32B×CD79b Bi-Specific Monovalent Fc Diabodies Inhibit Human Primary B Cell Proliferation In order to further demonstrate the ability of the CD32B× CD79b Fc diabodies of the present invention to dampen or inhibit the immune system, the above-described preferred CD32B×CD79b Fc diabody was incubated in the presence of primary human B cells obtained from two donors. Proliferation was monitored by the uptake of $^3$H-TdR after 48 hours in the presence of goat anti-human IgM Fc µ F(ab)$_2$ (5 µg/ml) and differing concentrations of either CD32B× CD79b Fc diabody or CD32B×CD79b ABD diabody. The results are shown in FIG. 3A (Donor 1) and FIG. 3B (Donor 2), and indicate a marked reduction in B cell proliferation in the presence of the CD32B×CD79b Fc diabody or the CD32B×CD79b (ABD) diabody.

Example 3

Figure 4A:
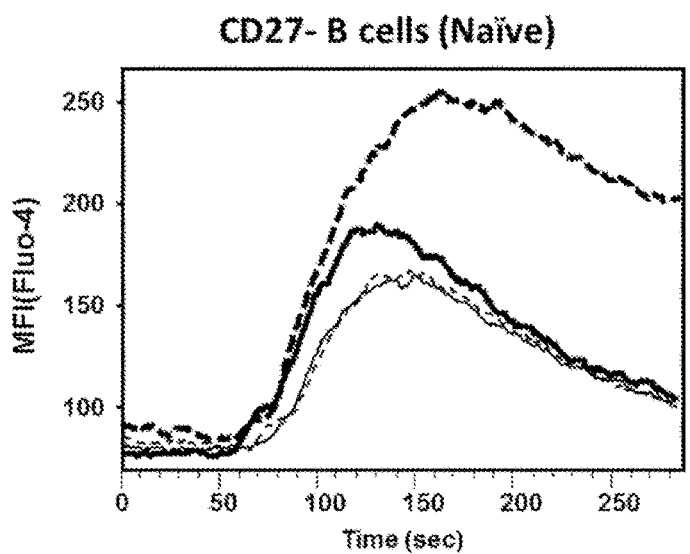
FIGS. 4A-4B show the ability of the preferred CD32B×CD79b Fc diabody, a non-Fc CD32B×CD79b (ABD) diabody, and a non-Fc CD32B×CD79b diabody to inhibit signaling in naïve (FIG. 4A) and memory (FIG. 4B) B cells.
Figure 4B:
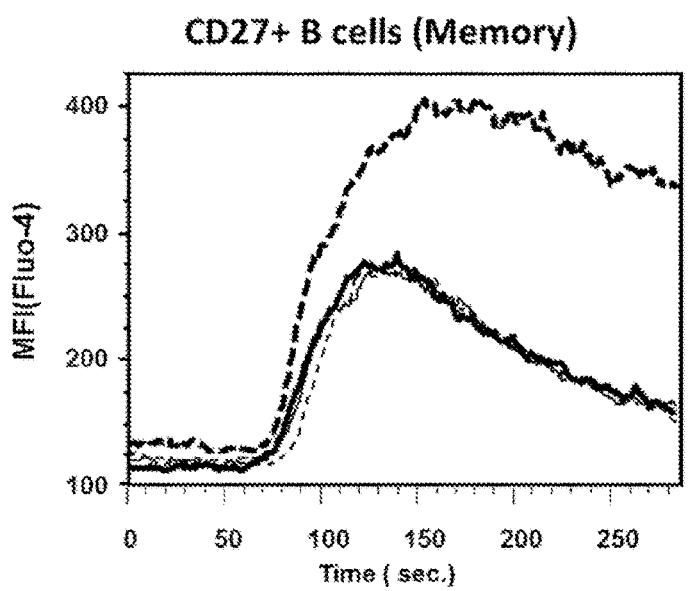

CD32B×CD79b Bi-Specific Monovalent Fc Diabodies Inhibit Signaling in Naïve and Memory B Cells In order to further demonstrate the ability of the CD32B× CD79b Fc diabodies of the present invention to dampen or inhibit signaling of the immune system by B cells, purified naïve or memory B cells were incubated for 30 minutes in the presence of goat anti-human IgM Fc µ (anti-µ) (30 µg/ml) alone or in the additional presence of the above-described preferred CD32B×CD79b Fc diabody. As seen in FIG. 4A (naïve B cells) and FIG. 4B (memory B cells), the presence of the preferred CD32B×CD79b Fc diabody, the CD32B×CD79b (ABD) diabody, or the CD32B×CD79b diabody all markedly reduced B cell signaling.

Example 4

CD32B×CD79b Bi-Specific Monovalent Fc Diabodies Inhibit Proliferation of SLE Patient B Cells In order to further demonstrate the ability of the CD32B× CD79b Fc diabodies of the present invention to dampen or inhibit signaling of the immune system by B cells, B cells of a patient suffering from systemic lupus erythematosus (SLE) were incubated in the presence of goat anti-human IgM Fc µ (anti-µ) alone or in the additional presence of the above-described preferred CD32B×CD79b Fc diabody. Proliferation was monitored by the uptake of $^3$H-TdR.

Figure 5A:
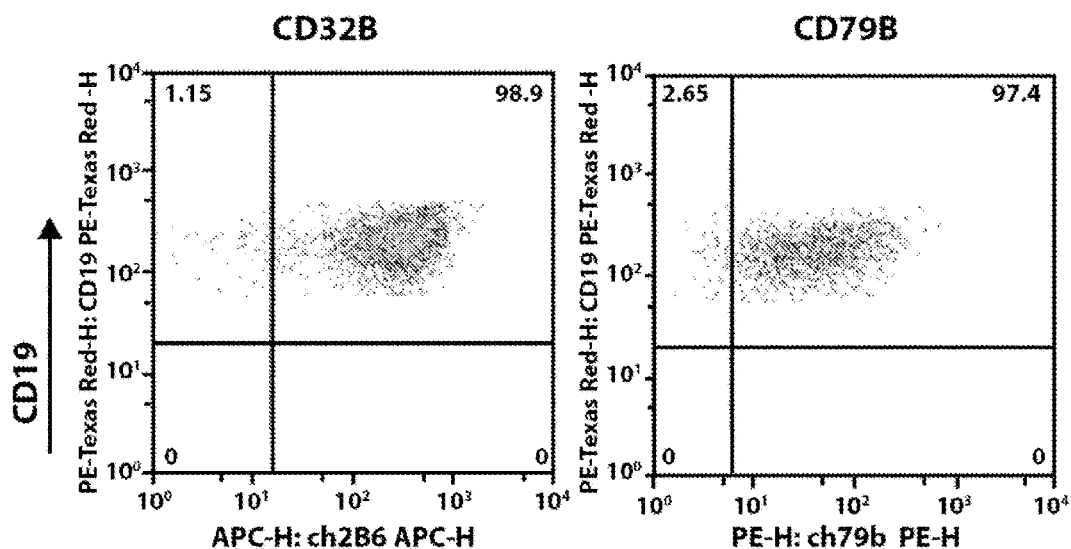
FIGS. 5A-5C show the ability of the preferred CD32B×CD79b Fc diabody or a non-Fc CD32B×CD79b (ABD) diabody to inhibit the proliferation of SLE cells. Such inhibition was found to be independent of disease status.
Figure 5B:
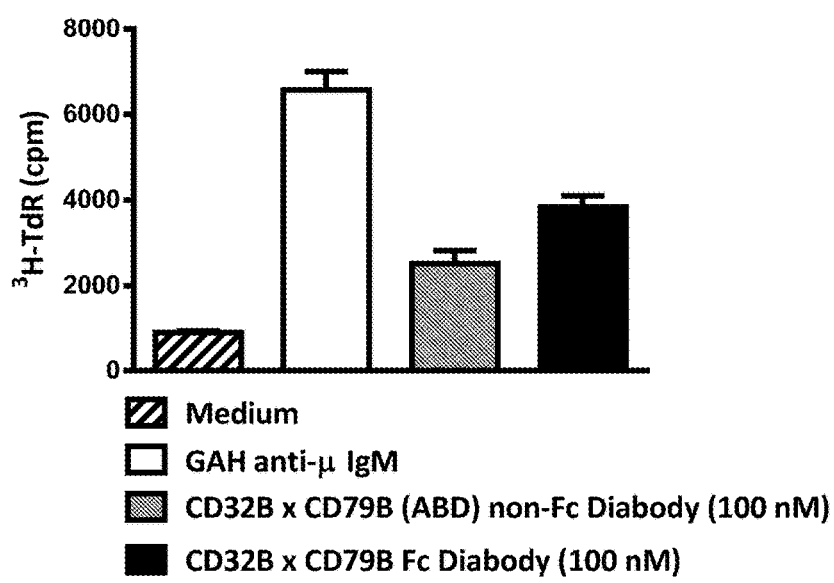

As shown in FIG. 5A, the above-described preferred CD32B×CD79b Fc diabody was found to be able to bind to both CD32B and CD79b. FIG. 5B, demonstrates that the provision of the goat anti-human IgM (GAH anti-µ) caused increased proliferation of the B cells, relative to the control, and that the additional administration of the above-described preferred CD32B×CD79b Fc diabody or the CD32B× CD79b (ABD) diabody markedly inhibit the extent of such proliferation.

Figure 5C:
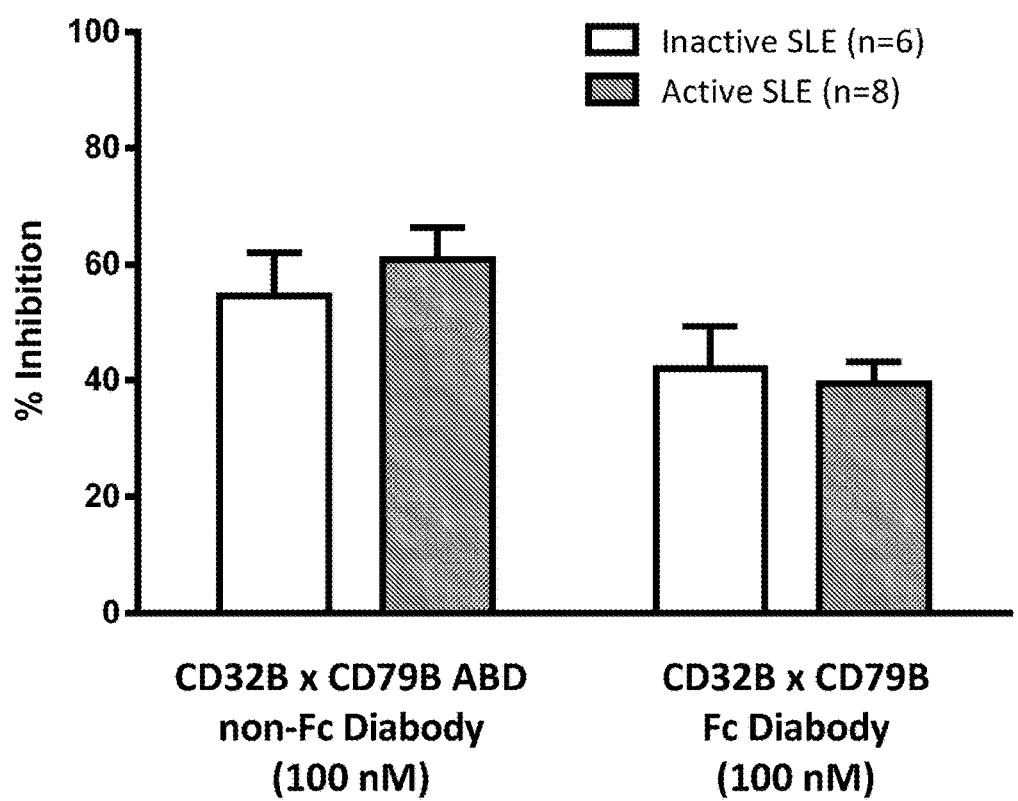

The capability of the above-described preferred CD32B× CD79b Fc diabody or of the CD32B×CD79b (ABD) diabody to decrease the extent of B cell proliferation of individuals suffering from SLE was found to be independent of the status of the disease. The extent of the reduction of B cell proliferation in patients with active or inactive SLE was approximately 40% relative to the proliferation observed in the presence of only the goat anti-human IgM (GAH anti-µ), and thus was irrespective of disease status (FIG. 5C). FIG. 5C further demonstrates that the preferred CD32B×CD79b Fc diabody provided greater inhibition than the CD32B× CD79b (ABD) diabody.

Example 5

CD32B×CD79b Bi-Specific Monovalent Fc Diabodies Modulate B Cell Responses In Vivo In order to further demonstrate the ability of the CD32B× CD79b Fc diabodies of the present invention to dampen or inhibit signaling of the immune system by B cells, human PBMC were injected into immunodeficient NSG mice (Agliano, A. et al. (2008) *"Human Acute Leukemia Cells Injected In NOD/Ltsz-Scid/IL-2Rgamma Null Mice Generate A Faster And More Efficient Disease Compared To Other NOD/Scid-Related Strains,"* Int. J. Cancer 123(9):2222-

2227; Sanchez, P. V. et al. (2009) *"A Robust Xenotransplantation Model For Acute Myeloid Leukemia,"* Leukemia 23(11):2109-2117; Racki, W. J. et al. (2010) *"NOD-Scid IL2rgamma(Null) Mouse Model Of Human Skin Transplantation And Allograft Rejection,"* Transplantation 89(5):527-536; Choi, B. et al. (2011) *"Human B Cell Development And Antibody Production In Humanized NOD/SCID/IL-2Rγ (Null) (NSG) Mice Conditioned By Busulfan,"* J. Clin. Immunol. 31(2):253-264; Sartelet, H. et al. (2012) *"Description Of A New Xenograft Model Of Metastatic Neuroblastoma Using NOD/SCID/Il2rg Null (NSG) Mice,"* In Vivo 26(1):19-29; Spranger, S. et al. (2012) *"NOD/scid IL-2Rg(null) Mice: A Preclinical Model System To Evaluate Human Dendritic Cell-Based Vaccine Strategies in vivo,"* J. Transl. Med. 10:30; von Bonin, M. et al. (2013) *"in vivo Expansion Of Co-Transplanted T Cells Impacts On Tumor Re-Initiating Activity Of Human Acute Myeloid Leukemia In NSG Mice,"* PLoS One. 8(4):e60680). Animals were administered a control vehicle (100 µl of phosphate buffered saline (PBS)/animal, q3d×2 weeks), the above-described preferred CD32B×CD79b Fc diabody (100 µl/animal, q3d×2 weeks), or a CD32B×CD79b diabody (composed of only two polypeptide strains and containing an albumin-binding domain). Plasma was assayed by ELISA at day 7 and day 14 for the presence of human IgM (FIG. 6A) or human IgG (FIG. 6B), both being indicative of the onset of graft vs. host disease.

Figure 6A:
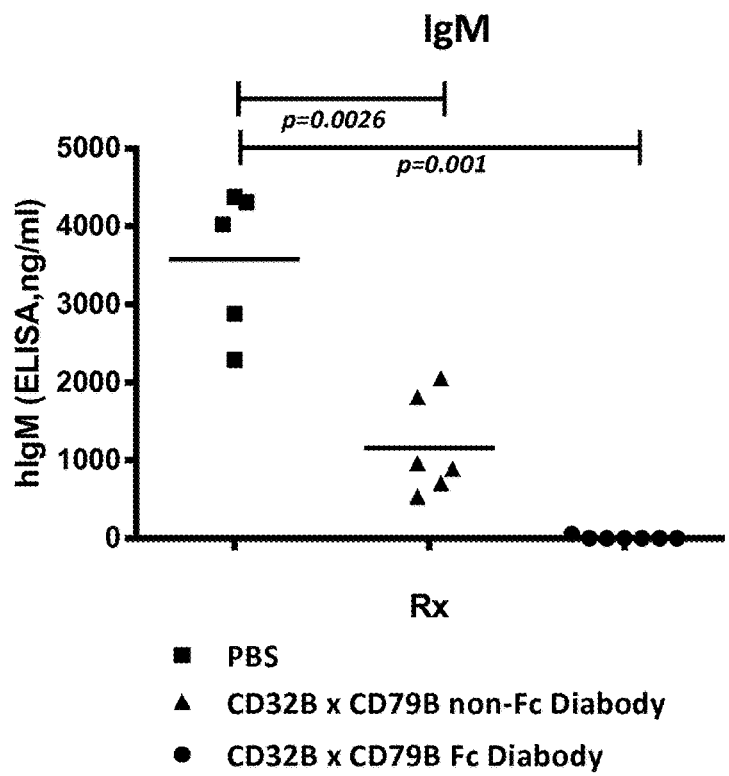
FIGS. 6A-6B show the ability of the preferred CD32B×CD79b Fc diabody or a non-Fc CD32B×CD79b diabody to modulate B cell responses in vivo, and demonstrate the unexpected superiority of the preferred CD32B×CD79b Fc diabody.
Figure 6B:
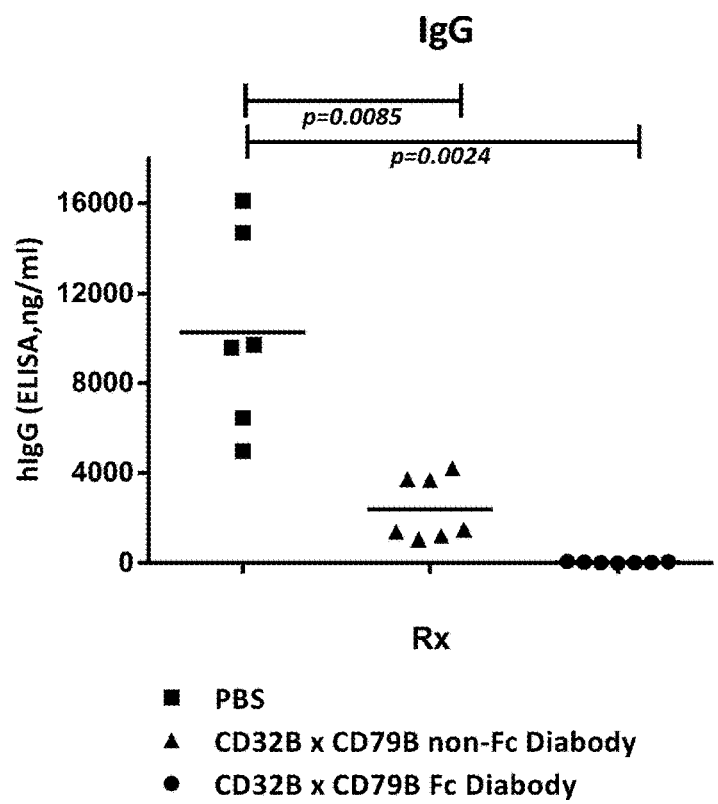

Mice receiving the control vehicle exhibited high levels of human IgM and human IgG. In contrast, such antibodies were essentially not detected in mice that had received the above-described preferred CD32B×CD79b Fc diabody (FIG. 6A and FIG. 6B). Mice that had received the CD32B×CD79b diabody exhibited diminished levels of human IgM and human IgG, compared to mice receiving the control vehicle, but such levels were nevertheless substantially higher than those receiving the CD32B×CD79b Fc diabody. These findings demonstrate that bi-specific monovalent CD32B×CD79b diabodies have therapeutic utility and effectiveness, but that the above-described preferred CD32B× CD79b Fc diabody of the present invention is unexpectedly superior to such non-Fc diabodies and possesses even greater therapeutic utility and effectiveness (FIG. 6A and FIG. 6B).

Example 6

Figure 7:
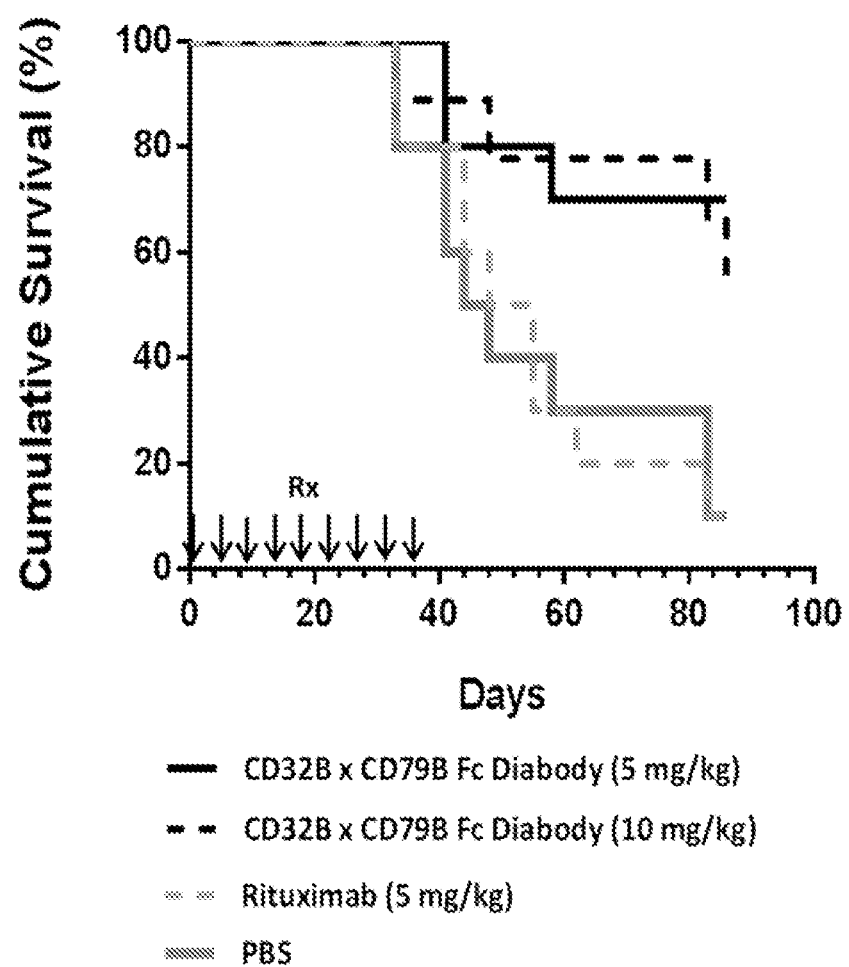
FIG. 7 shows the ability of the preferred CD32B×CD79b Fc diabody to decrease xenogeneic GvHD in the mouse.

CD32B×CD79b Bi-Specific Monovalent Fc Diabodies Decrease Xenogeneic GvHD in the Mouse In order to further demonstrate the ability of the CD32B× CD79b Fc diabodies of the present invention to dampen or inhibit signaling of the immune system by B cells, human PBMC ($5 \times 10^6$ cells, intravenously injected) were injected into immunodeficient NOD.scid IL2rγnull NSG mice. Animals were administered a control vehicle (100 µl of phosphate buffered saline (PBS)/animal), the above-described preferred CD32B×CD79b Fc diabody (at either 5 mg/kg or at 10 mg/kg) or an anti-CD20 antibody (rituximab; 5 mg/kg; dosed once). The cumulative survival of the mice was measured over time. As shown in FIG. 7, animals receiving either dose of the preferred CD32B×CD79b Fc diabody exhibited markedly enhanced survival; relative to mice receiving either the PCS control or rituximab.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A bi-specific monovalent Fc diabody, wherein said bi-specific monovalent Fc diabody is capable of specific binding to an epitope of CD32B and to an epitope of CD79b, and possesses an IgG Fc Domain, wherein the bi-specific monovalent Fc diabody comprises a first polypeptide chain, a second polypeptide chain and a third polypeptide chain, wherein said first and second polypeptide chains are covalently bonded to one another and said first and third polypeptide chains are covalently bonded to one another, and wherein:

A. the first polypeptide chain comprises, in the N-terminal to C-terminal direction:
   i. a Domain 1, comprising:
      (1) a sub-Domain (1A), which comprises a cysteine-containing peptide (SEQ ID NO:1); and
      (2) a sub-Domain (1B), which comprises a polypeptide portion of an IgG Fc Domain having CH2 and CH3 domains of an IgG immunoglobulin Fc region, wherein said sub-Domain (1B) comprises the amino acid sequence of SEQ ID NO:9 or the amino acid sequence of SEQ ID NO:10;
   ii. a Domain 2, comprising:
      (1) a sub-Domain (2A), which comprises a VL Domain of a monoclonal antibody capable of binding to CD32B (VL$_{CD32B}$) (SEQ ID NO:11); and
      (2) a sub-Domain (2B), which comprises a VH Domain of a monoclonal antibody capable of binding to CD79b (VH$_{CD79b}$) (SEQ ID NO:14), wherein said sub-Domains (2A) and (2B) are separated from one another by a peptide linker (Linker 2) (SEQ ID NO:4);
   iii. a Domain 3, wherein said Domain 3 is an E-coil Domain (SEQ ID NO:7) or a K-coil Domain (SEQ ID NO:8), wherein said Domain 3 is separated from said Domain 2 by a peptide linker (SEQ ID NO:5); and
   iv. a C-terminal spacer peptide (SEQ ID NO:6);

B. the second polypeptide chain comprises, in the N-terminal to C-terminal direction:
   i. a Domain 1, comprising:
      (1) a sub-Domain (1A), which comprises a VL Domain of a monoclonal antibody capable of binding to CD79b (VL$_{CD79b}$) (SEQ ID NO:13); and
      (2) a sub-Domain (1B), which comprises a VH Domain of a monoclonal antibody capable of binding to CD32B (VH$_{CD32B}$) (SEQ ID NO:12);
      wherein said sub-Domains (1A) and (1B) are separated from one another by a peptide linker (Linker 2) (SEQ ID NO:4);
   ii. a Domain 2, wherein said Domain 2 is a K-coil Domain (SEQ ID NO:8) or an E-coil Domain (SEQ ID NO:7), wherein said Domain 2 is separated from said Domain 1 by a peptide linker (SEQ ID NO:5); and wherein said Domain 3 of said first polypeptide chain and said Domain 2 of said second polypeptide chain are not both E-coil Domains or both K-coil Domains; and C. the third polypeptide chain comprises, in the N-terminal to C-terminal direction, a Domain 1 comprising:
   (1) a sub-Domain (1A), which comprises a cysteine-containing peptide (SEQ ID NO:1); and
   (2) a sub-Domain (1B), which comprises a polypeptide portion of an IgG Fc Domain having CH2 and CH3 domains of an IgG immunoglobulin Fc region, and wherein:
      (i) if said sub-Domain (1B) of said first polypeptide chain comprises the amino acid sequence of SEQ ID NO:9, said sub-Domain (1B) of said third polypeptide chain comprises the amino acid sequence of SEQ ID NO:10; or
(ii) if said sub-Domain (1B) of said first polypeptide chain comprises the amino acid sequence of SEQ ID NO:10, said sub-Domain (1B) of said third polypeptide chain comprises the amino acid sequence of SEQ ID NO:9;

and wherein:
(a) said polypeptide portions of the IgG Fc Domains of said first and third polypeptide chain form said IgG Fc Domain;
(b) said VL Domain of said first polypeptide chain and said VH Domain of said second polypeptide chain form an Antigen-Binding Domain capable of specific binding to an epitope of CD32B; and
(c) said VH Domain of said first polypeptide chain and said VL Domain of said second polypeptide chain form an Antigen-Binding Domain capable of specific binding to an epitope of CD79b.

2. The bi-specific monovalent Fc diabody of claim 1, wherein said sub-Domain (1B) of said first polypeptide chain comprises the amino acid sequence of SEQ ID NO:9, and said sub-Domain (1B) of said third polypeptide chain comprises the amino acid sequence of SEQ ID NO:10.

3. The bi-specific monovalent Fc diabody of claim 1, wherein said sub-Domain (1B) of said first polypeptide chain comprises the amino acid sequence of SEQ ID NO:10, and said sub-Domain (1B) of said third polypeptide chain comprises the amino acid sequence of SEQ ID NO:9.

4. The bi-specific monovalent Fc diabody of claim 1, wherein said Domain 1 of said first polypeptide chain and/or said Domain 1 of said third polypeptide chain comprises a variant CH2-CH3 sequence that exhibits altered binding to an Fcγ receptor.

5. The bi-specific monovalent Fc diabody of claim 1, wherein said Domain 3 of said first polypeptide chain comprises an E-coil (SEQ ID NO:7), and said Domain 2 of said second polypeptide chain comprises a K-coil (SEQ ID NO:8).

6. The bi-specific monovalent Fc diabody of claim 1, wherein said Domain 3 of said first polypeptide chain comprises a K-coil (SEQ ID NO:8), and said Domain 2 of said second polypeptide chain comprises an E-coil (SEQ ID NO:7).

7. A bi-specific monovalent Fc diabody, wherein said bi-specific monovalent Fc diabody is capable of specific binding to an epitope of CD32B and to an epitope of CD79b, and possesses an IgG Fc Domain, wherein said bi-specific monovalent Fc diabody comprises:
(1) a first polypeptide chain comprising the amino acid sequence of SEQ ID NO:15;
(2) a second polypeptide chain comprising the amino acid sequence of SEQ ID NO:16; and
(3) a third polypeptide chain comprising the amino acid sequence of SEQ ID NO:17, wherein amino acid residues 1-10 of said third polypeptide chain are Peptide 1 (SEQ ID NO:1), and amino acid residues 11-227 of said third polypeptide chain are the CH2 and CH3 domains of an IgG antibody Fc region (SEQ ID NO:10);
wherein said first and said second polypeptide chains are covalently bonded to one another by a first disulfide bond and said first and third polypeptide chains are covalently bonded to one another by a second disulfide bond.

8. A pharmaceutical composition comprising the bi-specific monovalent Fc diabody of claim 1 and a physiologically acceptable carrier.

9. A pharmaceutical composition comprising the bi-specific monovalent Fc diabody of claim 7 and a physiologically acceptable carrier.

* * * * *